(12) United States Patent
Zarins et al.

(10) Patent No.: US 9,023,037 B2
(45) Date of Patent: May 5, 2015

(54) BALLOON CATHETER APPARATUS FOR RENAL NEUROMODULATION

(71) Applicants: Denise Zarins, Saratoga, CA (US); Hanson Gifford, III, Woodside, CA (US); Mark Deem, Mountain View, CA (US); Nicolas Zadno, Fremont, CA (US); Benjamin J. Clark, Redwood City, CA (US); Andrew Wu, Mountain View, CA (US); Kenneth J. Michlitsch, Los Altos Hills, CA (US)

(72) Inventors: Denise Zarins, Saratoga, CA (US); Hanson Gifford, III, Woodside, CA (US); Mark Deem, Mountain View, CA (US); Nicolas Zadno, Fremont, CA (US); Benjamin J. Clark, Redwood City, CA (US); Andrew Wu, Mountain View, CA (US); Kenneth J. Michlitsch, Los Altos Hills, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 13/868,426

(22) Filed: Apr. 23, 2013

(65) Prior Publication Data

US 2013/0296767 A1 Nov. 7, 2013

Related U.S. Application Data

(63) Continuation of application No. 13/620,173, filed on Sep. 14, 2012, now Pat. No. 8,444,640, which is a continuation of application No. 11/599,890, filed on Nov. 14, 2006, now Pat. No. 8,347,891, which is a
(Continued)

(51) Int. Cl.
*A61B 18/12* (2006.01)
*A61B 18/18* (2006.01)
(Continued)

(52) U.S. Cl.
CPC ............ *A61B 18/18* (2013.01); *A61N 1/0551* (2013.01); *A61N 1/32* (2013.01); *A61N 1/327* (2013.01);
(Continued)

(58) Field of Classification Search
USPC ....................................... 606/49–52
See application file for complete search history.

(56) References Cited

U.S. PATENT DOCUMENTS

| 2,130,758 A | 9/1938 | Rose |
| 2,276,995 A | 3/1942 | Milinowski |

(Continued)

FOREIGN PATENT DOCUMENTS

| CN | 101583323 | 11/2009 |
| CN | 202386778 | 8/2012 |

(Continued)

OTHER PUBLICATIONS

U.S. Appl. No. 60/813,589, filed Dec. 29, 2005, Demarais et al.
(Continued)

*Primary Examiner* — Aaron Roane

(57) ABSTRACT

Methods and apparatus are provided for non-continuous circumferential treatment of a body lumen. Apparatus may be positioned within a body lumen of a patient and may deliver energy at a first lengthwise and angular position to create a less-than-full circumferential treatment zone at the first position. The apparatus also may deliver energy at one or more additional lengthwise and angular positions within the body lumen to create less-than-full circumferential treatment zone(s) at the one or more additional positions that are offset lengthwise and angularly from the first treatment zone. Superimposition of the first treatment zone and the one or more additional treatment zones defines a non-continuous circumferential treatment zone without formation of a continuous circumferential lesion. Various embodiments of methods and apparatus for achieving such non-continuous circumferential treatment are provided.

16 Claims, 11 Drawing Sheets

Related U.S. Application Data continuation-in-part of application No. 11/129,765, filed on May 13, 2005, now Pat. No. 7,653,438, which is a continuation-in-part of application No. 10/408,665, filed on Apr. 8, 2003, now Pat. No. 7,162,303, said application No. 11/599,890 is a continuation-in-part of application No. 11/189,563, filed on Jul. 25, 2005, now Pat. No. 8,145,316, which is a continuation-in-part of application No. 11/129,765, filed on May 13, 2005, now Pat. No. 7,653,438, said application No. 11/189,563 is a continuation-in-part of application No. 10/900,199, filed on Jul. 28, 2004, now Pat. No. 6,978,174, which is a continuation-in-part of application No. 10/408,665, filed on Apr. 8, 2003, now Pat. No. 7,162,303.

(60) Provisional application No. 60/616,254, filed on Oct. 5, 2004, provisional application No. 60/624,793, filed on Nov. 2, 2004, provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61N 1/32* (2006.01)
*A61N 1/36* (2006.01)
*A61B 18/14* (2006.01)
*A61N 1/05* (2006.01)
*A61N 7/02* (2006.01)
*A61B 18/00* (2006.01)

(52) U.S. Cl.
CPC .......... *A61N 1/36007* (2013.01); *A61N 7/022* (2013.01); *A61B 18/1492* (2013.01); *A61B 2018/0022* (2013.01); *A61B 2018/00267* (2013.01); *A61B 2018/00404* (2013.01); *A61B 2018/00434* (2013.01); *A61B 2018/00511* (2013.01); *A61B 18/1206* (2013.01)

(56) References Cited

U.S. PATENT DOCUMENTS

| | | | |
|---|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler et al. |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,531,943 A | 7/1985 | Van Tassel et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,709,698 A | 12/1987 | Johnston et al. |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,890,623 A | 1/1990 | Cook et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,078,717 A | 1/1992 | Parins et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,190,540 A | 3/1993 | Lee |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker, Jr. et al. |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,345,936 A | 9/1994 | Pomeranz et al. |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |

(56) References Cited

U.S. PATENT DOCUMENTS

| | | |
|---|---|---|
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,425,364 A | 6/1995 | Imran |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,465,717 A | 11/1995 | Imran et al. |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,496,311 A | 3/1996 | Abele et al. |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko et al. |
| 5,531,778 A | 7/1996 | Maschino et al. |
| 5,540,679 A | 7/1996 | Fram et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens et al. |
| 5,584,863 A | 12/1996 | Rauch et al. |
| 5,588,964 A | 12/1996 | Imran et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,687,737 A | 11/1997 | Branham et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,860,974 A | 1/1999 | Abele |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu et al. |
| 5,893,885 A | 4/1999 | Webster, Jr. |
| 5,899,860 A * | 5/1999 | Pfeiffer et al. ................. 600/424 |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,661 A * | 9/1999 | Greenspon et al. ........... 600/510 |
| 5,954,719 A | 9/1999 | Chen et al. |
| 5,983,131 A | 11/1999 | Weaver et al. |
| 5,983,141 A | 11/1999 | Sluijter et al. |
| 6,004,269 A | 12/1999 | Crowley et al. |
| 6,006,134 A | 12/1999 | Hill et al. |
| 6,009,877 A | 1/2000 | Edwards |
| 6,010,613 A | 1/2000 | Walters et al. |
| 6,024,740 A | 2/2000 | Lesh et al. |
| 6,026,326 A | 2/2000 | Bardy |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,091,995 A | 7/2000 | Ingle et al. |
| 6,110,192 A | 8/2000 | Ravenscroft et al. |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,146,380 A | 11/2000 | Racz et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,238,702 B1 | 5/2001 | Berde et al. |
| 6,245,026 B1 | 6/2001 | Campbell et al. |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |

(56) References Cited

U.S. PATENT DOCUMENTS

| | | | |
|---|---|---|---|
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,500,174 B1 | 12/2002 | Maguire et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,562,034 B2 | 5/2003 | Edwards et al. |
| 6,564,096 B2 | 5/2003 | Mest |
| 6,571,127 B1 | 5/2003 | Ben-Haim et al. |
| 6,575,933 B1 | 6/2003 | Wittenberger et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,490 B1 | 2/2004 | Edwards |
| 6,692,738 B2 | 2/2004 | MacLaughlin et al. |
| 6,697,670 B2 | 2/2004 | Chomenky et al. |
| 6,711,444 B2 | 3/2004 | Koblish |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,748,255 B2 | 6/2004 | Fuimaono et al. |
| 6,749,598 B1 | 6/2004 | Keren et al. |
| 6,752,805 B2 | 6/2004 | Maguire et al. |
| 6,780,183 B2 | 8/2004 | Jimenez, Jr. et al. |
| 6,786,904 B2 | 9/2004 | Doscher et al. |
| 6,795,728 B2 | 9/2004 | Chornenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,885,888 B2 | 4/2005 | Rezai |
| 6,916,656 B2 | 7/2005 | Walters et al. |
| 6,926,716 B2 | 8/2005 | Baker et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,958,060 B2 | 10/2005 | Mathiesen et al. |
| 6,964,660 B2 | 11/2005 | Maguire et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,291,146 B2 | 11/2007 | Steinke et al. |
| 7,373,204 B2 | 5/2008 | Gelfand et al. |
| 7,444,183 B2 | 10/2008 | Knudson et al. |
| 7,556,628 B2 * | 7/2009 | Utley et al. ............ 606/41 |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,756,583 B2 | 7/2010 | Demarais et al. |
| 8,019,435 B2 | 9/2011 | Hastings et al. |
| 8,131,371 B2 | 3/2012 | Demarals et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,295,902 B2 | 10/2012 | Salahieh et al. |
| 8,401,650 B2 | 3/2013 | Simon et al. |
| 8,444,640 B2 | 5/2013 | Demarais et al. |
| 8,666,496 B2 | 3/2014 | Simon et al. |
| 8,740,895 B2 | 6/2014 | Mayse et al. |
| 8,758,334 B2 | 6/2014 | Coe et al. |
| 8,777,943 B2 | 7/2014 | Mayse et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050637 A1 | 3/2003 | Maguire et al. |
| 2003/0050681 A1 | 3/2003 | Pianca et al. |
| 2003/0060848 A1 | 3/2003 | Kieval et al. |

(56) References Cited

U.S. PATENT DOCUMENTS

| | | |
|---|---|---|
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0144658 A1 | 7/2003 | Schwartz et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0229340 A1 | 12/2003 | Sherry et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096647 A1 | 5/2005 | Steinke et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251116 A1 | 11/2005 | Steinke et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0100618 A1 | 5/2006 | Chan et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0182873 A1 | 8/2006 | Klisch et al. |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235286 A1 | 10/2006 | Stone et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0125772 A1 | 5/2008 | Stone et al. |
| 2008/0140150 A1 | 6/2008 | Zhou et al. |
| 2008/0161801 A1 | 7/2008 | Steinke et al. |
| 2008/0188912 A1 | 8/2008 | Stone et al. |
| 2008/0188913 A1 | 8/2008 | Stone et al. |
| 2008/0213331 A1 | 9/2008 | Gelfand et al. |
| 2008/0255642 A1 | 10/2008 | Zarins et al. |
| 2008/0262489 A1 | 10/2008 | Steinke |
| 2008/0319513 A1 | 12/2008 | Pu et al. |
| 2009/0024195 A1 | 1/2009 | Rezai et al. |
| 2009/0036948 A1 | 2/2009 | Levin et al. |

(56) References Cited

U.S. PATENT DOCUMENTS

| | | |
|---|---|---|
| 2009/0062873 A1 | 3/2009 | Wu et al. |
| 2009/0076409 A1 | 3/2009 | Wu et al. |
| 2010/0010567 A1 | 1/2010 | Deem et al. |
| 2010/0057150 A1 | 3/2010 | Demarais et al. |
| 2010/0076299 A1 | 3/2010 | Gustus et al. |
| 2010/0125239 A1 | 5/2010 | Perry et al. |
| 2010/0125268 A1 | 5/2010 | Gustus et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0168743 A1 | 7/2010 | Stone et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0060324 A1 | 3/2011 | Wu et al. |
| 2011/0112400 A1 | 5/2011 | Emery et al. |
| 2011/0130708 A1 | 6/2011 | Perry et al. |
| 2011/0137298 A1 | 6/2011 | Nguyen et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0257622 A1 | 10/2011 | Salahieh et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0306851 A1 | 12/2011 | Wang |
| 2012/0029496 A1 | 2/2012 | Smith |
| 2012/0029500 A1 | 2/2012 | Jenson |
| 2012/0029509 A1 | 2/2012 | Smith |
| 2012/0029511 A1 | 2/2012 | Smith et al. |
| 2012/0029512 A1 | 2/2012 | Willard et al. |
| 2012/0071870 A1 | 3/2012 | Salahieh et al. |
| 2012/0095461 A1 | 4/2012 | Herscher et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0184952 A1 | 7/2012 | Jenson et al. |
| 2012/0191083 A1 | 7/2012 | Moll et al. |
| 2012/0271277 A1 | 10/2012 | Fischell et al. |
| 2012/0296232 A1 | 11/2012 | Ng |
| 2012/0296329 A1 | 11/2012 | Ng |
| 2013/0012866 A1 | 1/2013 | Deem et al. |
| 2013/0012867 A1 | 1/2013 | Demarais et al. |
| 2013/0035681 A1 | 2/2013 | Subramaniam et al. |
| 2013/0053732 A1 | 2/2013 | Heuser |
| 2013/0085493 A1 | 4/2013 | Bloom et al. |
| 2013/0090649 A1 | 4/2013 | Smith et al. |
| 2013/0116687 A1 | 5/2013 | Willard |
| 2013/0123778 A1 | 5/2013 | Richardson et al. |
| 2013/0165916 A1 | 6/2013 | Mathur et al. |
| 2013/0165917 A1 | 6/2013 | Mathur et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172881 A1 | 7/2013 | Hill et al. |
| 2013/0231658 A1 | 9/2013 | Wang et al. |
| 2013/0231659 A1 | 9/2013 | Hill et al. |
| 2013/0253628 A1 | 9/2013 | Smith et al. |
| 2013/0274658 A1 | 10/2013 | Steinke et al. |
| 2013/0282084 A1 | 10/2013 | Mathur et al. |
| 2013/0289555 A1 | 10/2013 | Mayse et al. |
| 2013/0289556 A1 | 10/2013 | Mayse et al. |
| 2013/0296853 A1 | 11/2013 | Sugimoto et al. |
| 2013/0304052 A1 | 11/2013 | Rizq et al. |
| 2013/0304054 A1 | 11/2013 | Zarins et al. |
| 2013/0304064 A1 | 11/2013 | Zarins et al. |
| 2014/0018794 A1 | 1/2014 | Anderson et al. |
| 2014/0018888 A1 | 1/2014 | Ostroot et al. |
| 2014/0058374 A1 | 2/2014 | Edmunds et al. |
| 2014/0058376 A1 | 2/2014 | Horn et al. |
| 2014/0066921 A1 | 3/2014 | Coe et al. |
| 2014/0066924 A1 | 3/2014 | Azamian et al. |
| 2014/0074083 A1 | 3/2014 | Horn et al. |
| 2014/0074089 A1 | 3/2014 | Nishii |
| 2014/0128859 A1 | 5/2014 | Lee |
| 2014/0135661 A1 | 5/2014 | Garrison et al. |
| 2014/0135715 A1 | 5/2014 | Lambert et al. |
| 2014/0135755 A1 | 5/2014 | Sutermeister et al. |
| 2014/0180077 A1 | 6/2014 | Huennekens et al. |
| 2014/0180196 A1 | 6/2014 | Stone et al. |
| 2014/0188103 A1 | 7/2014 | Millett |
| 2014/0200578 A1 | 7/2014 | Groff et al. |
| 2014/0243821 A1 | 8/2014 | Salahieh et al. |

FOREIGN PATENT DOCUMENTS

| | | |
|---|---|---|
| DE | 3151180 | 8/1982 |
| DE | 29909082 | 7/1999 |
| DE | 10252325 | 5/2004 |
| DE | 10257146 | 6/2004 |
| DE | 20 2004 021 941 | 5/2013 |
| DE | 20 2004 021 942 | 5/2013 |
| DE | 20 2004 021 949 | 5/2013 |
| DE | 20 2004 021 951 | 6/2013 |
| DE | 20 2004 021 952 | 6/2013 |
| DE | 20 2004 021 953 | 6/2013 |
| DE | 20 2004 021 944 | 7/2013 |
| EP | 0811395 | 12/1997 |
| EP | 1667595 | 6/2006 |
| EP | 1865870 | 12/2007 |
| EP | 1948301 | 7/2008 |
| EP | 1009303 | 6/2009 |
| EP | 2076193 | 7/2009 |
| EP | 2076194 | 7/2009 |
| EP | 2076198 | 7/2009 |
| EP | 2091455 | 8/2009 |
| EP | 2092957 | 8/2009 |
| EP | 2341839 | 7/2011 |
| EP | 2352542 | 8/2011 |
| EP | 2355737 | 8/2011 |
| EP | 2370015 | 10/2011 |
| EP | 2429641 | 3/2012 |
| EP | 2438877 | 4/2012 |
| EP | 2452648 | 5/2012 |
| EP | 2455034 | 5/2012 |
| EP | 2455035 | 5/2012 |
| EP | 2455036 | 5/2012 |
| EP | 2519173 | 11/2012 |
| EP | 2555699 | 2/2013 |
| EP | 2558016 | 2/2013 |
| EP | 2568905 | 3/2013 |
| EP | 2598068 | 6/2013 |
| EP | 2598070 | 6/2013 |
| EP | 2598071 | 6/2013 |
| EP | 2656807 | 10/2013 |
| EP | 2694150 | 2/2014 |
| EP | 2694158 | 2/2014 |
| EP | 2701795 | 3/2014 |
| EP | 2731531 | 5/2014 |
| EP | 2755588 | 7/2014 |
| EP | 2760532 | 8/2014 |
| JP | 2010509032 | 3/2010 |
| WO | WO-85/01213 | 3/1985 |
| WO | WO-91/04725 | 4/1991 |
| WO | WO-9211898 | 7/1992 |
| WO | WO-9220291 | 11/1992 |
| WO | WO-93/02740 | 2/1993 |
| WO | WO-93/07803 | 4/1993 |
| WO | WO-94/00188 | 1/1994 |
| WO | WO-94/11057 | 5/1994 |

(56) References Cited

FOREIGN PATENT DOCUMENTS

| | | |
|---|---|---|
| WO | WO-9510319 | 4/1995 |
| WO | WO-95/25472 | 9/1995 |
| WO | WO-9531142 | 11/1995 |
| WO | WO-95/33514 | 12/1995 |
| WO | WO-96/00039 | 1/1996 |
| WO | WO-96/04957 | 2/1996 |
| WO | WO 96/11723 | 4/1996 |
| WO | WO-9634559 | 11/1996 |
| WO | WO-97/13463 | 4/1997 |
| WO | WO-97/13550 | 4/1997 |
| WO | WO-9736548 | 10/1997 |
| WO | WO-97/49453 | 12/1997 |
| WO | WO-98/37926 | 9/1998 |
| WO | WO-98/42403 | 10/1998 |
| WO | WO-98/43700 | 10/1998 |
| WO | WO-98/43701 | 10/1998 |
| WO | WO-98/48888 | 11/1998 |
| WO | WO-9900060 | 1/1999 |
| WO | WO-99/33407 | 7/1999 |
| WO | WO-9942047 | 8/1999 |
| WO | WO-99/51286 | 10/1999 |
| WO | WO-99/52424 | 10/1999 |
| WO | WO-9962413 | 12/1999 |
| WO | WO-01/26729 | 4/2001 |
| WO | WO-0122897 | 4/2001 |
| WO | WO-0170114 | 9/2001 |
| WO | WO-02/09808 | 2/2002 |
| WO | WO-02/26314 | 4/2002 |
| WO | WO-02/053207 | 7/2002 |
| WO | WO-02/070039 | 9/2002 |
| WO | WO-02/070047 | 9/2002 |
| WO | WO-02/085448 | 10/2002 |
| WO | WO-02085192 | 10/2002 |
| WO | WO-03/018108 | 3/2003 |
| WO | WO-03/028802 | 4/2003 |
| WO | WO-03/063692 | 8/2003 |
| WO | WO-03/071140 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005/014100 | 2/2005 |
| WO | WO-2005/016165 | 2/2005 |
| WO | WO-2005/032646 | 4/2005 |
| WO | WO-2005030072 | 4/2005 |
| WO | WO-2005037070 | 4/2005 |
| WO | WO-2005041748 | 5/2005 |
| WO | WO-2005/065284 | 7/2005 |
| WO | WO-2005/084389 A2 | 9/2005 |
| WO | WO-2005/097256 A2 | 10/2005 |
| WO | WO-2005/110528 A1 | 11/2005 |
| WO | WO-2005107623 | 11/2005 |
| WO | WO-2005/123183 | 12/2005 |
| WO | WO-2006/007048 A2 | 1/2006 |
| WO | WO-2006/018528 A1 | 2/2006 |
| WO | WO-2006/022790 | 3/2006 |
| WO | WO-2006/031899 | 3/2006 |
| WO | WO-2006041847 | 4/2006 |
| WO | WO-2006041881 | 4/2006 |
| WO | WO-2006105121 | 10/2006 |
| WO | WO-2007008954 | 1/2007 |
| WO | WO-2007035537 | 3/2007 |
| WO | WO-2007078997 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008049082 | 4/2008 |
| WO | WO-2008049084 | 4/2008 |
| WO | WO-2008049087 | 4/2008 |
| WO | WO-2008061150 | 5/2008 |
| WO | WO-2008061152 | 5/2008 |
| WO | WO-2008070413 | 6/2008 |
| WO | WO-2009121017 | 10/2009 |
| WO | WO-2010033940 | 3/2010 |
| WO | WO-2010056745 | 5/2010 |
| WO | WO-2010057043 | 5/2010 |
| WO | WO-2010078175 | 7/2010 |
| WO | WO-2010132703 | 11/2010 |
| WO | WO-2011082278 | 7/2011 |
| WO | WO-2011082279 | 7/2011 |
| WO | WO-2011119857 | 9/2011 |
| WO | WO-2011126580 | 10/2011 |
| WO | WO-2011130534 | 10/2011 |
| WO | WO-2011143468 | 11/2011 |
| WO | WO-2012016135 | 2/2012 |
| WO | WO-2012016137 | 2/2012 |
| WO | WO-2012075156 | 6/2012 |
| WO | WO-2012122157 | 9/2012 |
| WO | WO-2012130337 | 10/2012 |
| WO | WO-2012131107 | 10/2012 |
| WO | WO-2012135703 | 10/2012 |
| WO | WO-2012161875 | 11/2012 |
| WO | WO-2012174375 | 12/2012 |
| WO | WO-2013013156 | 1/2013 |
| WO | WO-2013028812 | 2/2013 |
| WO | WO-2013040201 | 3/2013 |
| WO | WO-2013049601 | 4/2013 |
| WO | WO-2013052590 | 4/2013 |
| WO | WO-2013055685 | 4/2013 |
| WO | WO-2013070724 | 5/2013 |
| WO | WO-2013077283 | 5/2013 |
| WO | WO-2013096913 | 6/2013 |
| WO | WO-2013096916 | 6/2013 |
| WO | WO-2013096919 | 6/2013 |
| WO | WO-2013096920 | 6/2013 |
| WO | WO-2013096922 | 6/2013 |
| WO | WO-2013101446 | 7/2013 |
| WO | WO-2013101452 | 7/2013 |
| WO | WO-2013112844 | 8/2013 |
| WO | WO-2013/131046 | 9/2013 |
| WO | WO-2013154775 | 10/2013 |
| WO | WO-2014022379 | 2/2014 |
| WO | WO-2014036160 | 3/2014 |
| WO | WO-2014056460 | 4/2014 |
| WO | WO-2014059165 | 4/2014 |
| WO | WO-2014071223 | 5/2014 |
| WO | WO-2014078301 | 5/2014 |
| WO | WO-2014096969 | 6/2014 |
| WO | WO-2014100226 | 6/2014 |
| WO | WO-2014110579 | 7/2014 |

OTHER PUBLICATIONS

2003 European Society of Hypertension—European Society of Cardiology guidelines for the management of arterial hypertension, Guidelines Committee, Journal of Hypertension 2003, vol. 21, No. 6, pp. 1011-1053.

Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.

Abramov, G.S. et al., Alteration in sensory nerve function following electrical shock, Burns vol. 22, No. 8, 1996 Elsevier Science Ltd., pp. 602-606.

Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.

Advanced Neuromodulation Systems' Comparison Chart, Dec. 16, 2008, pp. 1.

Advances in the role of the sympathetic nervous system in cardiovascular medicine, 2001 SNS Report, No. 3, Springer, Published with an educational grant from Servier, pp. 1-8.

Aggarwal, A. et al., Regional sympathetic effects of low-dose clonidine in heart failure. Hypertension. 2003;41:553-7.

(56) References Cited

OTHER PUBLICATIONS

Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.

Ahadian, Farshad M., M.D., Pulsed Radiofrequency Neurotomy: Advances in Pain Medicine, Current Pain and Headache Reports 2004, vol. 8, 2004 Current Science Inc., pp. 34-40.

Alexander, B.T. et al., Renal denervation abolishes hypertension in low-birth-weight offspring from pregnant rats with reduced uterine perfusion, Hypertension, 2005; 45 (part 2): pp. 754-758.

Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.

Allen, E.V., Sympathectomy for essential hypertension, Circulation, 1952, 6:131-140.

Amersham Health. Hypaque-Cysto, 2003, 6 pages.

Andrews, B.T. et al., The use of surgical sympathectomy in the treatment of chronic renal pain. Br J Urol. 1997; 80: 6-10.

Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.

Archer, Steffen et al., Cell Reactions to Dielectrophoretic Manipulation, Mar. 1, 1999, Biochemical and Biophysical Research Communications, 1999 Academic Press, pp. 687-698.

Arentz, T. et al., Incidence of pulmonary vein stenosis 2 years after radiofrequency catheter ablation of refractory atrial fibrillation. European Heart Journal. 2003. 24; pp. 963-969.

Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.

Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.

Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.

Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.

Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.

Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.

Badyal, D. K., H. Lata and A.P. Dadhich, Animal Models of Hypertension and Effect of Drugs, Aug. 19, 2003, Indian Journal of Pharmacology 2003, vol. 35, pp. 349-362.

Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.

Balazs, Tibor, Development of Tissue Resistance to Toxic Effects of Chemicals, Jan. 26, 1974, Toxicology, 2 (1974), Elsevier/North-Holland, Amsterdam, pp. 247-255.

Barajas, L. Innervation of the renal cortex. Fex Proc. 1978;37:1 192-201.

Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.

Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.

Bassett, C. Andrew L. et al., Augmentation of Bone Repair by Inductively Coupled Electromagnetic Fields, May 3, 1974, Science, vol. 184, pp. 575-577.

Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.

Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.

Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.

Bello-Reuss, E. et al., Acute unilateral renal denervation in rats with extracellular volume expansion, Departments of Medicine and Physiology, University of North Carolina School of Medicine. F26-F32 Jul. 1975.

Bello-Reuss, E. et al., Effect of renal sympathetic nerve stimulation on proximal water and sodium reabsorption, J Clin Invest, 1976;57:1104-1107.

Bello-Reuss, E. et al., Effects of Acute Unilateral Renal Denervation in the Rat, J Clin Invest, 1975;56:208-217.

Berde, C. et al., Local Anesthetics, Anesthesia, Chapter 13, 5th addition, Churchill-Livingston, Philadelphia 2000, pp. 491-521.

Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.

Bhandari, A. and Ellias, M., Loin pain hematuria syndrome: Pain control with RFA to the Splanchanic plexus, The Pain Clinic, 2000, vol. 12, No. 4, pp. 323-327.

Bhatt, Deepak L. et al., Rhabdomyolysis Due to Pulsed Electric Fields, May 11, 1989, Plastic and Reconstructive Surgery Jul. 1990, pp. 1-11.

Bichet, D., et al., Renal intracortical blood flow and renin secretion after denervation by 6-hydroxydopamine. Can J Physiol Pharmacol. 1982;60:184-92.

Bigler, D. et al., Tachyphylaxis during postoperative epidural analgesia—new insights, Apr. 15, 1987, Letter to the Editor, Acta Anaesthesiol Scand. 1987, vol. 31, pp. 664-665.

Binder, Allan et al., Pulsed Electromagnetic Field Therapy of Persistent Rotator Cuff Tendinitis, The Lancet, Saturday Mar. 31, 1984, The Lancet Ltd., pp. 695-698.

Black, M.D., Henry R., Resistant Hypertension 2004, presentation at Rush University Medical Center, Jul. 15, 2004, 40 pages.

Blad, B., et al., An Electrical Impedance index to Assess Electroporation in Tissue, Tissue and Organ (Therapy), 2001, Oslo, www.bl.uk <http://www.bl.uk> British Library, pp. 31-34.

Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.

Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.

Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.

Bourge, R.C., Heart Failure Monitoring Devices: Rationale and Status 28 pages, Feb. 2001.

Braunwald, E., Heart Disease, A Textbook of Cardiovascular Medicine, 5th Ed., vol. 2, 1997, pp. 480-481, 824-825, 1184-1288 and 1923-1925, W.B. Saunders Company.

Bravo, E.L., et al., Renal denervation for resistant hypertension, American Journal of Kidney Diseases, 2009, 3 pgs.

(56) References Cited

OTHER PUBLICATIONS

Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;1 15:1999-2005.
Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.
Campese, V.M. et al., Renal Afferent Denervation Prevents the Progression of Renal Disease in the Renal Ablation Model of Chronic Renal Failure in the Rat, Am J Kidney Dis. 1995;26:861-5.
Campese, V.M., a new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.
Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, 1997 WB Saunders Company, pp. 480-481.
Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment for Chronic Heart Failure: Electrical Modulation of Myocardial Contractility. Transcatheter Cardiovascular Therapeutics 2005, 21 slides.
Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
Clinical Trials in Hypertension and Renal Diseases, Slide Source, www.hypertensiononline.org, 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.
Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Curtis, J.J. et al., Surgical theray for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.
Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.
Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.
Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
Dibona, Gerald F. and Susan Y. Jones, Dynamic Analysis of Renal Nerve Activity Responses to Baroreceptor Denervation in

(56) References Cited

OTHER PUBLICATIONS

Hypertensive Rats, Sep. 19, 2000, Hypertension Apr. 2001, American Heart Association, Inc. 2001, pp. 1153-1163.
Dibona, Gerald F. and Ulla C. Kopp, Neural Control of Renal Function, Physiological Reviews, vol. 77, No. 1, Jan. 1997, the American Physiological Society 1997, pp. 75-197.
Dibona, Gerald F. and Ulla C. Kopp, Role of the Renal Sympathetic Nerves in Pathophysiological States, Neural Control of Renal Function, vol. 77, pp. 142-197 Jan. 1997.
Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.
DiBona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
Dibona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
Dibona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.
Dibona, Gerald F., Sympathetic Nervous System and the Kidney in Hypertension, Current Opinion in Nephrology and Hypertension 2002, vol. 11, 2002 Lippincott Williams & Wilkins, pp. 197-200.
Dibona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.
Dibona, Gerald, LL Sawin, Effect of renal denervation on dynamic autoregulation of renal blood flow, Feb. 12, 2004, AmJ Physiol Renal Physiol 286, pp. F1209-F1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.
Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 Apr. 2000, National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, A Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev Arat-Ozkan, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; Date of Mailing: Jan. 19, 2010, 4 pgs.
European Examination Report; European Patent Application No. 09156661.2; Applicant: Ardian, Inc.; Date of Mailing: Jan. 19, 2010, 6 pgs.
European Search Report; European Patent Application No. 05806045.0; Applicant: Ardian, Inc.; Date of Mailing: Sep. 22, 2009, 8 pgs.
European Search Report; European Patent Application No. 05811851.4; Applicant: Ardian, Inc.; Date of Mailing: Oct. 1, 2009, 7 pgs.
European Search Report; European Patent Application No. 06847926.0; Applicant: Ardian, Inc.; Date of Mailing: Feb. 10, 2010, 6 pgs.
European Search Report; European Patent Application No. 07757925.8; Applicant: Ardian, Inc.; Date of Mailing: Apr. 29, 2010, 9 pgs.
European Search Report; European Patent Application No. 07798341.9; Applicant: Ardian, Inc.; Date of Mailing Aug. 4, 2011; 6 pgs.
European Search Report; European Patent Application No. 07799148.7; Applicant: Ardian, Inc.; Date of Mailing: Jul. 23, 2009, 6 pgs.
European Search Report; European Patent Application No. 07868755.5; Applicant: Ardian, Inc.; Date of Mailing: Jul. 28, 2010, 7 pgs.
European Search Report; European Patent Application No. 09156661.2; Applicant: Ardian, Inc.; Date of Mailing: Jul. 23, 2009, 6 pgs.
European Search Report; European Patent Application No. 09167937.3; Applicant: Ardian, Inc.; Date of Mailing: Nov. 11, 2009, 6 pgs.
European Search Report; European Patent Application No. 09168202.1; Applicant: Ardian, Inc.; Date of Mailing: Nov. 11, 2009, 5 pgs.
European Search Report; European Patent Application No. 09168204.7; Applicant: Ardian, Inc.; Date of Mailing: Nov. 19, 2009, 6 pgs.
Evelyn, K.A. et al., Effect of thoracolumbar sympathectomy on the clinical course of primary (essential) hypertension, Am J Med, 1960;28:188-221.
*Ex parte Quayle Office Action*; U.S. Appl. No. 11/144,173; Mailed on May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.

(56) References Cited

OTHER PUBLICATIONS

Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.
Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; Mailed on Jan. 29, 2009, 11 pgs.
Final Office Action; U.S. Appl. No. 11/266,993; Mailed on Jan. 8, 2010, 7 pgs.
Final Office Action; U.S. Appl. No. 11/363,867; Mailed on May 1, 2009, 8 pgs.
Final Office Action; U.S. Appl. No. 11/451,728; Mailed on Jan. 13, 2009, 7 pgs.
Final Office Action; U.S. Appl. No. 11/599,649; Mailed on Jan. 15, 2009, 10 pgs.
Final Office Action; U.S. Appl. No. 11/599,723; Mailed on Apr. 5, 2010, 17 pgs.
Final Office Action; U.S. Appl. No. 11/599,890; Mailed on Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.
Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.
Gattone II, Vincent H. et al., Contribution of Renal Innervation to Hypertension in Polycystic Kidney Disease in the Rat, University of Chicago Section of Urology, 16 pages, Mar. 17, 2008.
Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.
Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.
Getts, R.T. et al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., the outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update. pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.
Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
Heart Disease and Stroke Statistics—2004 Update, American Heart Association, American Stroke Association, Dallas, Texas, 2003 American Heart Association, 52 pgs.
Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104 (4): 771-786.
Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.

(56) References Cited

OTHER PUBLICATIONS

Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.
Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.
Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.
Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.
Norwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.
Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.
Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.
Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.
Hypertension and Renal Disease: Mechanisms, Slide Show by www.hypertensiononline.org, 22 pages Mar. 30, 2001.
Hypertension Incidence and Prevalence, Age-Specific Rates, by Gender, B.C., 2001/2002, Graph, Chronic Disease Management, May 2003, British Columbia Ministry of Health Services, 1 page.
Implantable Neurostimulation Systems, Medtronic Neurological, http://medtronic.com/neuro/paintherapies/pain_treatment_ladder/pdf/implantable_brochure.pdf 1999, 6 pages.
Implantable Pump—The Medtronic MiniMed 2007 Implantable Insulin Pump System, Medtronic MiniMed 2006, 5 pgs.
International Search Report and Written Opinion for PCT/US2009/069334; Applicant: Ardian, Inc.; Mailing Date: Mar. 1, 2010, 10 pgs.
International Search Report and Written Opinion, PCT/US05/35693, Mailed on Mar. 8, 2006, Applicant: Ardian, Inc., 29 pgs.
International Search Report and Written Opinion, PCT/US05/35757, Mailed on Dec. 27, 2006, Applicant: Ardian, Inc., 8 pgs.
International Search Report and Written Opinion, PCT/US06/36120, Mailed on Jun. 25, 2008, Applicant: Ardian, Inc., 10 pgs.
International Search Report and Written Opinion, PCT/US06/41889, Mailed on Oct. 20, 2008, Applicant: Ardian, Inc., 7 pgs.
International Search Report and Written Opinion, PCT/US06/48822, Mailed on Aug. 15, 2008, Applicant: Ardian, Inc. 12 pgs.
International Search Report and Written Opinion, PCT/US07/633222, Mailed on Mar. 3, 2008, Applicant: Ardian, Inc. 10 pgs.
International Search Report and Written Opinion, PCT/US07/63324, Mailed on Oct. 10, 2008, Applicant: Ardian, Inc. 10 pgs.
International Search Report and Written Opinion, PCT/US07/66539, Mailed on Jan. 28, 2008, Applicant: Ardian, Inc. 6 pgs.
International Search Report and Written Opinion, PCT/US07/70799, Mailed on Jul. 2, 2008, Applicant: Ardian, Inc., 7 pgs.
International Search Report and Written Opinion, PCT/US07/72396, Mailed on Aug. 27, 2008, Applicant: Ardian, Inc. 9 pgs.
International Search Report and Written Opinion, PCT/US07/84701, Mailed on Aug. 21, 2008, Applicant: Ardian, Inc. 11 pgs.
International Search Report and Written Opinion, PCT/US07/84705, Mailed on Jul. 28, 2008, Applicant: Ardian, Inc., 12 pgs.
International Search Report and Written Opinion, PCT/US07/84708, Mailed on Aug. 11, 2008, Applicant: Ardian, Inc., 9 pgs.
International Search Report, PCT/US02/0039, Mailed Sep. 11, 2002, Applicant: Advanced Neuromodulation Systems, Inc.
International Search Report, PCT/US02/25712, Mailed on Apr. 23, 2003, Applicant: Cyberonics, Inc.
International Search Report, PCT/US03/08014, Mailed on Sep. 23, 2003, Applicant: The General Hospital Corporation.
International Search Report, PCT/US03/09764, Mailed on Oct. 28, 2003, Applicant: CVRX, Inc.
International Search Report, PCT/US04/38498, Mailed Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121 ;pp. 989-1001. 1998.
Jia, Jianping et al., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.
Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II): II-166-II-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.

(56) References Cited

OTHER PUBLICATIONS

Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by the American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.
Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, SLEEP 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SPORTSMed. Connecticut State Medical Society Committee on the Medical Aspects of Sports. Fall/Winter 2005. 10 pgs.
Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.
Lee, Raphael C. et al., Clinical Sequelae Manifested in Electrical Shock Survivors, Presentation by the Electrical Trauma Research Program, The University of Chicago, 37 pages Dec. 24, 2004.
Lee, Raphael C. et al., Membrane Biology and Biophysics, Chapter 25, Surgical Research, 2001 Academic Press, pp. 297-305.
Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.
Lenoble, L.M. et al., Selective efferent chemical sympathectomy of rat kidneys. Am J Physiol. 1985;249:R496-501.
Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.
Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.
Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.
Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.
Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.
Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.
Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.
Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.
Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.
Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.
Luippold, G. et al., Chronic renal denervation prevents glomerular hyperfiltration in diabetic rats, Nephrol Dial Transplant (2004) 19:342-347.
Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.
Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.
Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.
Mancia, G., Grassi, G., Giannattasio, C., Seravalle, G., Sympathetic actrivation of pathogenesis of hypertension and progression of organ damage, Hypertension 1999, 34 (4 Pt 2): 724-728.

(56) References Cited

OTHER PUBLICATIONS

Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.
Market for infusion pumps grows with an aging population, NWL 97-01, The BBI Newsletter, vol. 20, No. 2, Feb. 1, 1997, American Health Consultants, Inc., pp. 6.
Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.
McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.
McCullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.
McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.
McRobbie, D. and M.A. Foster, Thresholds for biological effects of time-varying magnetic fields, Dec. 16, 1983, Clin. Phys. Physiol. Meas. 1984, vol. 5, No. 2, 1984 the Institute of Physics, pp. 67-78.
Medtronic Inc., MiniMed 2007, Implantable Insulin Pump System (Shoreview, MN) 4 pgs.
Medtronic Neurostimulation Systems, Expanding the Array of Pain Control Solutions, informational pamphlet, 1999 Medtronic, Inc., 6 pages.
Medtronic, Spinal Cord Stimulation, Patient Management Guidelines for Clinicians, Medtronic, Inc. 1999, 115 pages.
Medtronic, SynchroMed Infusion System—Clinical Reference Guide for Pain Therapy, Medtronic, Inc. 1998, 198 pages.
Mehran, Roxana, Renal insufficiency and contrast nephropathy: The most common, least understood risk factor, Cardiovascular Research Foundation, Columbia University Medical Center, 2005, 86 slides.
Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.
Micro ETS Hyperhidrosis USA Hyperhidrosis USA. 2 pgs. <URL: http://www.hyperhidrosis-usa.com/Index.html>. Nov. 6, 2006.
Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. ½, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine Hci) Injection, Rx only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You At Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; Mailed on Mar. 21, 2006, 14 pgs.
Non-Final Office Action; U.S. Appl. No. 11/129,765; Mailed on May 18, 2007, 10 pgs.
Non-Final Office Action; U.S. Appl. No. 11/129,765; Mailed on Sep. 10, 2007, 5 pgs.
Non-Final Office Action; U.S. Appl. No. 11/129,765; Mailed on Oct. 6, 2006, 30 pgs.
Non-Final Office Action; U.S. Appl. No. 11/133,925; Mailed on Oct. 8, 2008, 41 pgs.
Non-Final Office Action; U.S. Appl. No. 11/144,173; Mailed on Apr. 5, 2007, 33 pgs.
Non-Final Office Action; U.S. Appl. No. 11/144,173; Mailed on Sep. 10, 2007, 5 pgs.
Non-Final Office Action; U.S. Appl. No. 11/144,298; Mailed Oct. 29, 2009, 8 pgs.
Non-Final Office Action; U.S. Appl. No. 11/144,298; Mailed on Apr. 5, 2007, 33 pgs.
Non-Final Office Action; U.S. Appl. No. 11/144,298; Mailed on Sep. 10, 2007, 5 pgs.
Non-Final Office Action; U.S. Appl. No. 11/144,298; Mailed on Dec. 29, 2008, 7 pgs.
Non-Final Office Action; U.S. Appl. No. 11/145,122; Mailed on Apr. 11, 2007, 33 pgs.
Non-Final Office Action; U.S. Appl. No. 11/145,122; Mailed on Sep. 10, 2007, 5 pgs.
Non-Final Office Action; U.S. Appl. No. 11/189,563; Mailed on May 28, 2009, 5 pgs.
Non-Final Office Action; U.S. Appl. No. 11/233,814; Mailed on Jun. 17, 2008, 12 pgs.
Non-Final Office Action; U.S. Appl. No. 11/252,462; Mailed on Feb. 22, 2010, 6 pgs.
Non-Final Office Action; U.S. Appl. No. 11/266,993; Mailed on Jul. 8, 2009, 5 pgs.
Non-Final Office Action; U.S. Appl. No. 11/266,993; Mailed on Dec. 30, 2008, 7 pgs.
Non-Final Office Action; U.S. Appl. No. 11/363,867; Mailed on Sep. 25, 2008, 10 pgs.
Non-Final Office Action; U.S. Appl. No. 11/368,553; Mailed on May 18, 2010, 4 pgs.
Non-Final Office Action; U.S. Appl. No. 11/368,553; Mailed on Oct. 7, 2009, 5 pgs.
Non-Final Office Action; U.S. Appl. No. 11/368,809; Mailed on Dec. 3, 2009, 4 pgs.
Non-Final Office Action; U.S. Appl. No. 11/368,949; Mailed on Jun. 11, 2010, 6 pgs.
Non-Final Office Action; U.S. Appl. No. 11/368,971; Mailed on Aug. 24, 2010, 9 pgs.
Non-Final Office Action; U.S. Appl. No. 11/451,728; Mailed on Jun. 12, 2008, 41 pgs.
Non-Final Office Action; U.S. Appl. No. 11/451,728; Mailed on Jul. 2, 2009, 5 pgs.
Non-Final Office Action; U.S. Appl. No. 11/451,728; Mailed on Dec. 28, 2009, 7 pgs.
Non-Final Office Action; U.S. Appl. No. 11/504,117; Mailed on Mar. 31, 2009, 10 pgs.
Non-Final Office Action; U.S. Appl. No. 11/599,649; Mailed on Mar. 30, 2009, 10 pgs.
Non-Final Office Action; U.S. Appl. No. 11/599,649; Mailed on Jun. 23, 2008, 9 pgs.
Non-Final Office Action; U.S. Appl. No. 11/599,723; Mailed on Jun. 26, 2009, 17 pgs.
Non-Final Office Action; U.S. Appl. No. 11/599,723; Mailed on Oct. 15, 2010, 16 pgs.

(56) References Cited

OTHER PUBLICATIONS

Non-Final Office Action; U.S. Appl. No. 11/599,882; Mailed on Jul. 6, 2009, 13 pgs.
Non-Final Office Action; U.S. Appl. No. 11/688,178; Mailed on Jun. 28, 2010, 5 pgs.
Non-Final Office Action; U.S. Appl. No. 11/840,142; Mailed on Apr. 3, 2009, 13 pgs.
Non-Final Office Action; U.S. Appl. No. 12/567,521; Mailed on Sep. 3, 2010, 9 pgs.
Non-Final Office Action; U.S. Appl. No. 12/616,708; Mailed Sep. 16, 2010, 10 pgs.
Non-Final Office Action; U.S. Appl. No. 12/725,375; Mailed on Oct. 12, 2010, 14 pgs.
Nozawa, T. et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1935;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.

Podhajsky R.J. et al, The Histologic Effects of Pulsed and Continuous Radiofrequency Lesions at 42 C to Rat Dorsal Root Ganglion and Sciatic Nerve, Spine, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. And Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.
Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.

(56) References Cited

OTHER PUBLICATIONS

Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.

Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.

Sabbah, Hani N., Animal Models for Heart Failure and Device Development, Henry Ford Health System. 24 slides, Oct. 17, 2005.

Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.

Schauerte, P et al., Catheter ablation of cardiac autonomic nerves for prevention of vagal atrial fibrillation, Circulation. 102(22). Nov. 28, 2000. Abstract only. 2 pgs.

Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.

Scheiner, Avram, Ph.D., The design, development and implementation of electrodes used for functional electrial stimulation, Thesis paper, Case Western Reserve University, May 1992, 220 pages.

Scherlag, BJ and Po, S., Yhe intrinsic cardiac nervous system and atrial fibrillation, Current Opinion in Cardiology. 21(1):51-54, Jan. 2006. Abstract only. 2 pgs.

Schlaich, M.P. et al., Relation between cardiac sympathetic activity and hypertensive left ventricular hypertrophy. Circulation. 2003;108:560-5.

Schlaich, M.P. et al., Sympathetic augmentation in hypertension: role of nerve firing, norepinephrine reuptake, and angiotensin neuromodulation, Hypertension, 2004, 43:169-175.

Schmitt, Joseph et al., Intravascular Optical Coherence Tomography—Opening a Window into Coronary Artery Disease, LightLab Imaging, Inc. Business Briefing: European Cardiology 2005.

Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.

Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.

Scremin, Oscar U., M.D., Ph.D. and Daniel P. Holschneider, M.D., 31 & 32.. An Implantable Bolus Infusion Pump for the Neurosciences, FRP, Apr. 2005, 3 pages.

Sensorcaine—MPF Spinal Injection, informational document, AstraZeneca 2001, 2 pgs.

Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.

Shannon, J.L. et al., Studies on the innervation of human renal allografts, J Pathol. 1998, vol. 186, pp. 109-115.

Shlipak, M.G. et al., The clinical challenge of cardiorenal syndrome. Circulation. 2004;1 10:1514-7.

Shupak, Naomi M., Therapeutic Uses of Pulsed Magnetic-Field Exposure: A Review, Radio Science Bulletin Dec. 2003, No. 307, pp. 9-32.

Shu-Qing, Liu et al., Old spinal cord injury treated by pulsed electric stimulation, General Hospital of Beijing Command, Beijing, Dec. 6, 1990, 5 pages (full article in Chinese; abstract on last page.).

Siegel, RJ et al., Clinical demonstration that catheter-delivered ultrasound energy reverses arterial vasoconstriction, Journal of the American College of Cardiology. 1992. 20; 732-735. Summary only. 2 pgs.

Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.

Sisken, B.F. et al., 229.17 Influence of Non-Thermal Pulsed Radiofrequency Fields (PRF) on Neurite Outgrowth, Society for Neuroscience, vol. 21, 1995, 2 pages.

Skeie, B. et al., Effect of chronic bupivacaine infusion on seizure threshold to bupivacaine, Dec. 28, 1986, Acta Anaesthesiol Scand 1987, vol. 31, pp. 423-425.

Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006.

Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.

Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.

Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.

Sluijter, M.D., Ph.D., Radiofrequency Part 2: Thoracic and Cervical Region, Headache and Facial Pain, various pages from, FlivoPress SA, Meggen (LU), Switzerland, 13 pages 2002.

Sluijter, M.D., Ph.D., The Role of Radiofrequency in Failed Back Surgery Patients, Current Review of Pain 2000, vol. 4, 2000 by Current Science Inc., pp. 49-53.

Smithwick, R.H. et al., Hypertension and associated cardiovascular disease: comparison of male and female mortality rates and their influence on selection of therapy, JAMA, 1956, 160:1023-1033.

Smithwick, R.H. et al., Splanchnicectomy for essential hypertension, Journal Am Med Assn, 1953;152:1501-1504.

Smithwick, R.H., Surgical treatment of hypertension, Am J Med 1948, 4:744-759.

Sobotka, Paul A., Treatment Strategies for Fluid Overload, CHF Patients, CHF Solutions. Transcatheter Cardiovascular Therapeutics 2005. 20 slides.

Solis-Herruzo, J.A. et al., Effects of lumbar sympathetic block on kidney function in cirrhotic patients with hepatorenal syndrome, Journal of Hepatology, 1987; 5: 167-173.

Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.

Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.

Steffen, W. et al., Catheter-delivered high intensity, low frequency ultrasound induces vasodilation in vivo, European Heart Journal. 1994. 15; pp. 369-376.

Steg, PG et al., Pulsed ultraviolet laser irradiation produces endothelium-independent relaxation of vascular smooth muscle, Circulation: Journal of the American Heart Association. 1989. pp. 189-197.

Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.

Strojek, K. et al., Lowering of microalbuminuria in diabetic patients by a sympathicoplegic agent: novel approach to prevent progression of diabetic nephropathy? J Am Soc Nephrol. 2001;12:602-5.

Summary, Critical Reviews in Biomedical Engineering, vol. 17, Issue 5, 1989, pp. 515-529.

Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.

(56) References Cited

OTHER PUBLICATIONS

Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.
Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.
Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.
Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.
Terashima, Mitsuyasu et al. Feasibility and Safety of a Novel CryoPlasty™ System. Poster. 1 page, Mar. 15, 2002.
Thatipelli et al., CT Angiography of Renal Artery Anatomy for Evaluating Embolic Protection Devices, Journal of Vascular and Interventional Radiology, Jul. 2007, pp. 842-846.
The Antihypertensive and Lipid-Lowering Treatment to Prevent Heart Attack Trial, ALLHAT Research Group, JAMA, 2002, vol. 288, pp. 2981-2997.
Thomas, John R. and Oakley, E. Howard N. Chapter 15: Nonfreezing Cold Injury Medical Aspects of Harsh Environments, vol. 1. pp. 467-490, 2001.
Thompson, Gregory W., et al., Bradycardia Induced by Intravascular Versus Direct Stimulation of the Vagus Nerve, Aug. 24, 1997, The Society of Thoracic Surgeons 1998, pp. 637-642.
Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.
Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.
Trapani, Angelo J. et al., Neurohumoral interactions in conscious dehydrated rabbit, Am. J. Physiol. 254, 1988, the American Physiological Society 1988, pp. R338-R347.
Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.
Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.
Trumble, Dennis R. and James A. MaGovern, Comparison of Dog and Pig Models for Testing Substernal Cardiac Compression Devices, Nov. 2003, ASAIO Journal 2004, pp. 188-192.
Tsai, E., Intrathecal drug delivery for pain indications, technique, results, Pain Lecture presentation, Jun. 8, 2001, 31 pages.
Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.
Valente, John F. et al., Laparoscopic renal denervation for intractable ADPKD-related pain, Aug. 24, 2000, Nephrol Dial Transplant 2001, vol. 16, European Renal Association—European Dialysis and Transplant Association, p. 160.
Van Antwerp, Bill and Poonam Gulati, Protein Delivery from Mechanical Devices Challenges and Opportunities, Medtronic presentation, 19 pages, Jul. 2003.
Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.
Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.
Villarreal, Daniel et al., Effects of renal denervation on postprandial sodium excretion in experimental heart failure, Oct. 29, 1993, Am J Physiol 266, 1994, pp. R1599-R1604.
Villarreal, Daniel et al., Neurohumoral modulators and sodium balance in experimental heart failure, Nov. 6, 1992, Am. J. Physiol, vol. 264, 1993, pp. H1187-H1193.
Vonend, O. et al., Moxonidine treatment of hypertensive patients with advanced renal failure. J Hypertens. 2003;21:1709-17.
Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.
Wald, Jan D., Ph.D, et al., Cardiology Update: 2003, Sep. 11, 2003, AG Edwards 2003, 120 pages.
Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.
Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.
Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.
Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, Oct. 1974, pp. 575-585.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.
Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, the American Journal of Cardiology vol. 93, Jun. 15, 2004, 2004 by Excerpta Medica, Inc., pp. 1526-1528.
Ye, Richard D., M.D., Ph.D., Pharmacology of the Peripheral Nervous System, E-425 MSB, 6 pages, Jan. 2000.
Ye, S. et al., A limited renal injury may cause a permanent form of neurogenic hypertension. Am J Hypertens. 1998;11:723-8.

(56) References Cited

OTHER PUBLICATIONS

Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.

Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.

Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.

Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.

Zanchetti, A. et al., Neural Control of the Kidney—Are There Reno-Renal Reflexes?, Clin. and Exper. Hyper. Theory and Practice, A6 (1&2), 1984, Marcel Dekker, Inc. 1984, pp. 275-286.

Zanchetti, A. et al., Practice Guidelines for Primary Care Physicians: 2003 ESH/ESC Hypertension Guidelines, Journal of Hypertension, vol. 21, No. 10, 2003, pp. 1779-1786.

Zanchetti, A.S., Neural regulation of renin release: Experimental evidence and clinical implications in arterial hypertension, Circulation, 1977, 56(5) 691-698.

Zimmermann, Ulrich, Electrical Breakdown, Electropermeabilization and Electrofusion, Rev. Physiol. Biochem. Pharmacol., vol. 105, Springer-Verlag 1986, pp. 175-256.

Zoccali, C. et al., Plasma norepinephrine predicts survival and incident cardiovascular events in patients with end-stage renal disease. Circulation. 2002;105:1354-9.

Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.

Zundert, Jan Van, M.D. Fipp and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter,"Journal of the American College of Cardiology, 1999; 33; pp. 972-984.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Schneider, Peter A., "Endovascular Skills—Guidewire and Catheter Skills for Endovascular Surgery," Second Edition Revised and Expanded, 10 pages, (2003).

Kandarpa, Krishna et al., "Handbook of Interventional Radiologic Procedures", Third Edition, pp. 194-210 (2002).

ThermoCool Irrigated Catheter and Integrated Ablation System, Biosense Webster (2006), 6 pages.

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP2092957, Granted Jan. 5, 2011, Date of Opposition Oct. 5, 2011, 26 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Oz, Mehmet, Pressure Relief, Time, Jan. 9, 2012, 2 pages. <www.time.come/time/printout/0,8816,2103278,00.html>.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Pulmonary Vein Stenosis Following Catheter Ablation of Atrial Fibrillation, Curr. Opin. Cardio. 20 :484-490, 2005.

Papademetriou, Vasilios, Renal Sympathetic Denervation for the Treatment of Difficult-to-Control or Resistant Hypertension, Int. Journal of Hypertension, 2011, 8 pages.

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.

"2011 Edison Award Winners." Edison Awards: Honoring Innovations & Innovators, 2011, 6 pages, <http://www.edisonawards.com/BestNewProduct_2011.php>.

"2012 top 10 advances in heart disease and stroke research: American Heart Association/America Stroke Association Top 10 Research Report." American Heart Association, Dec. 17, 2012, 5 pages, attp://newsroom.heart.org/news/2012-top-10-advances-in-heart-241901>.

"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.

"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages.

(56) References Cited

OTHER PUBLICATIONS

<http://www.cxyascular.com/in-latest-news/interventional-news—latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards[TM]" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Intery Cardiac Electrophysiol, 2:285-292 (1998).
Final Office Action; U.S. Appl. No. 12/827,700; Mailed on Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery ebolization with diluted hot contrast medium: An experimental study." J Vasc Intery Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot[TM] renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.

(56) References Cited

OTHER PUBLICATIONS

Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
European Search Report dted May 3, 2012; European Patent Application No. 11192511.1; Applicant: Ardain, Inc.; 6 pages.
European Search Report dated May 3, 2012; European Patent Application No. 11192514.5; Applicant: Ardian, Inc.; 7 pages.
European Search Report dated Jan. 30, 2013; European Application No. 12180426.4; Applicant: Medtronic Ardian Luxembourg S.a.r.I.; 6 pages.
European Search Report dated Feb. 28, 2013; European Application No. 12180427.2; Applicant: Medtronic Ardian Luxembourg S.a.r.I.; 4 pages.
European Search Report dated Jan. 30, 2013; Application No. 12180428.0; Applicant: Medtronic Ardian Luxembourg S.a.r.I.; 6 pages.
European Search Report dated Jan. 30, 2013; Application No. 12180430.6; Applicant: Medtronic Ardian Luxembourg S.a.r.I.; 6 pages.
European Search Report dated Jan. 30, 2013; Application No. 12180431.4; Applicant: Medtronic Ardian Luxembourg S.a.r.I.; 6 pages.
European Search Report dated Feb. 22, 2013; Application No. 12180432.2; Applicant: Medtronic Ardian Luxembourg S.a.r.I.; 6 pages.
Eick, Olaf, "Temperature Controlled Radiofrequency Ablation." Indian Pacing and Electrophysiology Journal, vol. 2. No. 3, 2002, 8 pages.
Pieper et al., "Design and implementation of a new computerized system for intraoperative cardiac mapping." the American Physiological Society. 1991, 12 pages.
European Search Report dated May 3, 2012; Application No. 11192511.1; Applicant: Ardian, Inc.; 6 pages.
International Search Report and Written Opinion for International App. No. PCT/US07/84708, Date mailed Aug. 11, 2008, 9 pages.
European Search Report for European Application No. 13159257, Date Mailed: Oct. 17, 2013, 7 pages.
European Search Report for European Application No. 13159256, Date Mailed: Oct. 17, 2013, 6 pages.
European Search Report for European Application No. 13159259, Date Mailed: Oct. 17, 2013, 7 pages.
Beale et al., "Minimally Invasive Treatment for Varicose Veins: A Review of Endovenous Laser Treatment and Radiofrequency Ablation". Lower Extremity Wounds 3(4), 2004, 10 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3:" Dubium Sapientiae Initium"(Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.

\* cited by examiner

BALLOON CATHETER APPARATUS FOR RENAL NEUROMODULATION

REFERENCE TO RELATED APPLICATION

The present application is a continuation of U.S. patent application Ser. No. 13/620,173, filed Sep. 14, 2012, now U.S. Pat. No. 8,444,640, which is a continuation of U.S. patent application Ser. No. 11/599,890, filed Nov. 14, 2006, now U.S. Pat. No. 8,347,891, which is a continuation-in-part application of each of the following patents and co-pending United States patent applications:

(1) U.S. patent application Ser. No. 11/129,765, filed May 13, 2005, now U.S. Pat. No. 7,653,438, which (a) claims the benefit of U.S. Provisional Patent Application Nos. 60/616,254, filed Oct. 5, 2004, and 60/624,793, filed Nov. 2, 2004; and (b) is a continuation-in-part of U.S. patent application Ser. No. 10/408,665, filed Apr. 8, 2003, now U.S. Pat. No. 7,162,303, which claims the benefit of U.S. Provisional Application Nos. 60/370,190 filed Apr. 8, 2002; 60/415,575, filed Oct. 3, 2002; and 60/442,970, filed Jan. 29, 2003.

(2) U.S. patent application Ser. No. 11/189,563 filed Jul. 25, 2005, now U.S. Pat. No. 8,145,316, which (a) is a continuation-in-part of U.S. patent application Ser. No. 11/129,765, filed May 13, 2005, now U.S. Pat. No. 7,653,438, which claims the benefit of U.S. Provisional Patent Application Nos. 60/616,254, filed Oct. 5, 2004, and 60/624,793, filed Nov. 2, 2004; and (b) is a continuation-in-part of U.S. patent application Ser. No. 10/900,199, filed Jul. 28, 2004, now U.S. Pat. No. 6,978,174, which is a continuation-in-part of U.S. patent application Ser. No. 10/408,665, filed Apr. 8, 2003, now U.S. Pat. No. 7,162,303, which claims the benefit of U.S. Provisional Application Nos. 60/370,190 filed Apr. 8, 2002; 60/415,575, filed Oct. 3, 2002; and 60/442,970, filed Jan. 29, 2003.

All the foregoing applications and patents are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for performing a non-continuous circumferential treatment of a body lumen. Several embodiments of such methods and apparatus are directed to circumferential treatments of the body lumen that apply energy in one or more discrete treatment areas to form one or more lesions that are not contiguous or continuous about any complete circumference of a cross-section normal to a longitudinal axis of the body lumen.

BACKGROUND

Applicants have described methods and apparatus for treating a variety of renal and cardio-renal diseases, such as heart failure, renal disease, renal failure, hypertension, contrast nephropathy, arrhythmia and myocardial infarction, by modulating neural fibers that contribute to renal function, e.g., denervating tissue containing the neural fibers that contribute to renal function. This is expected to reduce renal sympathetic nervous activity, which increases removal of water and sodium from the body, and returns renin secretion to more normal levels. Normalized renin secretion causes blood vessels supplying the kidneys to assume a steady state level of dilation/constriction, which provides adequate renal blood flow. See, for example, Applicants' U.S. Pat. Nos.: (a) 7,162,303; (b) 7,653,438; (c) 8,145,316; (d) 7,620,451; (e) 7,617,005; and (f) 6,978,174. All of these applications and the patent are incorporated herein by reference in their entireties.

Applicants also have previously described methods and apparatus for intravascularly-induced neuromodulation or denervation of an innervated blood vessel in a patient or any target neural fibers in proximity to a blood vessel, for example, to treat any neurological disorder or other medical condition. Nerves in proximity to a blood vessel may innervate an effector organ or tissue. Intravascularly-induced neuromodulation or denervation may be utilized to treat a host of neurological disorders or other medical conditions, including, but not limited to, the aforementioned conditions including heart failure and hypertension, as well as pain and peripheral arterial occlusive disease (e.g., via pain mitigation). The methods and apparatus may be used to modulate efferent or afferent nerve signals, as well as combinations of efferent and afferent nerve signals. See, for example, Applicants' co-pending U.S. Patent Application Publication No. US 2007/0129760, which is incorporated herein by reference in its entirety.

Although the foregoing methods are useful by themselves, one challenge of neuromodulation and/or denervation is sufficiently affecting the neural tissue from within the vessel. For example, intravascular neuromodulation should avoid increasing the risk of acute and/or late stenosis. Therefore, it would be desirable to provide methods and apparatus that further address these challenges.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

Figure 1:
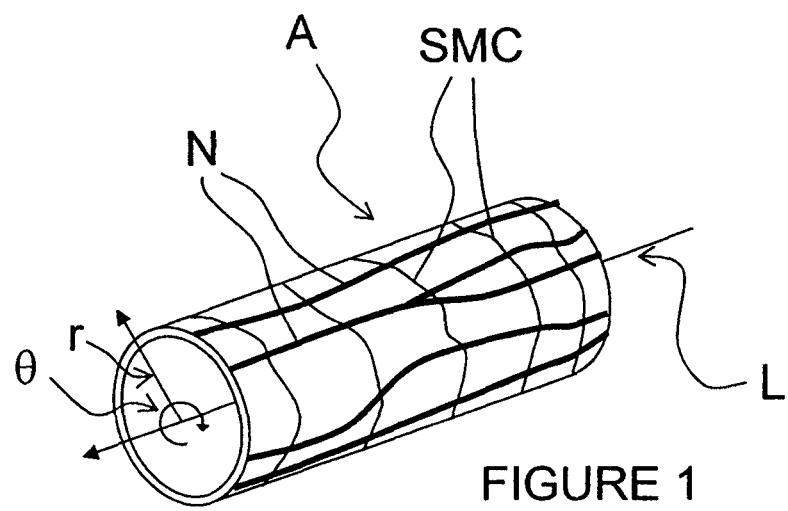
FIG. 1 is a schematic isometric detail view showing a common location of neural fibers proximate an artery.

The applicants have discovered that it may be desirable to perform a circumferential treatment of a body lumen to positively affect a medical condition by applying energy to discrete zones that are non-continuous along the complete circumference of a radial cross-section generally normal to the lumen wall. For example, in the treatment of atrial fibrillation or other arrhythmia, a circumferential treatment may be achieved by forming a continuous circumferential lesion that is continuous completely about a normal cross-section of the pulmonary vein to disrupt aberrant electrical signals. In the treatment of heart failure, a circumferential treatment may be achieved by forming a similar continuous circumferential lesion that is continuous completely about a normal cross-section of a renal artery to reduce renal sympathetic neural activity. However, continuous circumferential lesions that extend continuously about a full 360° of the circumference of a cross-section normal to the body lumen or tissue in proximity to the body lumen may increase a risk of acute and/or late stenosis formation within the blood vessel. Therefore, many of the embodiments described below are directed to forming discrete, non-continuous lesions normal of a lumen without adversely affecting the vessel.

Such non-continuous treatments may, for example, be conducted from an intravascular or intraluminal position, which can include treatment utilizing elements passed from an intravascular location to an extravascular location, i.e., intra-to-extravascular treatment. However, it should be understood that extravascular treatment apparatus and methods in accordance with the present invention also may be provided.

The treatments can be applied relative to nerves, including nervous tissue in the brain, or other target structures within or in proximity to a blood vessel or other body lumen that travel at least generally parallel or along a lengthwise dimension of the blood vessel (body lumen). The target structures can additionally or alternatively comprise a rotational orientation relative to the blood vessel (body lumen). Several disclosed embodiments of non-continuous circumferential treatments may reduce the risk of acute and/or late stenosis formation by treating neural matter along portions of multiple radial planes or cross-sections that are normal to, and spaced apart along, the lengthwise or longitudinal axis of the blood vessel (body lumen).

The treatment area at each radial plane or cross-section defines a treatment zone that is not completely continuous along a normal circumference, i.e., defines a treatment zone without a continuous circumferential lesion normal to the longitudinal axis. However, superimposition of the multiple treatment zones along the multiple radial planes or normal cross-sections defines a non-continuous, overlapping circumferential treatment zone along a lengthwise or longitudinal segment of the blood vessel (body lumen). In some embodiments, this overlapping treatment zone may provide a non-continuous, but substantially fully circumferential treatment without formation of a continuous circumferential lesion normal to the vessel (lumen). In other embodiments, the overlapping treatment zone may provide a non-continuous, partial circumferential treatment.

In this manner, a non-continuous circumferential treatment is performed over a lengthwise segment of the blood vessel (body lumen), as compared to a continuous circumferential treatment at a single normal cross-section or radial plane. Target structures substantially traveling along the lengthwise dimension of the blood vessel (body lumen) are thus circumferentially affected in a non-continuous fashion without formation of the continuous circumferential lesion along any normal cross-section or radial plane of the blood vessel (body lumen). This may reduce a risk of acute or late stenosis formation within the blood vessel (body lumen). A non-continuous circumferential treatment can thus comprise a treatment conducted at multiple positions about the lengthwise dimension of a body lumen, wherein the treatment zone at any one lengthwise position does not comprise a continuous circumferential lesion completely about a radial plane or normal cross-section, but wherein a superimposition of the treatment zones at all or some of the lengthwise positions may define an overlapping circumferential treatment zone.

The non-continuous circumferential treatment optionally may be achieved via apparatus positioned within a body lumen in proximity to target neural fibers for application of energy to the target neural fibers. The treatment may be induced, for example, via electrical and/or magnetic energy application, via thermal energy application (either heating or cooling), via mechanical energy application, via chemical energy application, via nuclear or radiation energy application, via fluid energy application, etc. Such treatment may be achieved, for example, via a thermal or non-thermal electric field, via a continuous or pulsed electric field, via a stimulation electric field, via localized drug delivery, via high intensity focused ultrasound, via thermal techniques, via athermal techniques, combinations thereof, etc. Such treatment may, for example, effectuate irreversible electroporation or electrofusion, necrosis and/or inducement of apoptosis, alteration of gene expression, action potential blockade or attenuation, changes in cytokine up-regulation, ablation and other conditions in target neural fibers. All or a part of the apparatus optionally may be passed through a wall of the body lumen to an extraluminal location in order to facilitate the treatment. The body lumen may, for example, comprise a blood vessel, and the apparatus may be positioned within the blood vessel via well-known percutaneous techniques.

Treatment may be achieved via either direct alteration of the target structures (e.g., target neural structures) or at least in part via alteration of the vascular or other structures that support the target structures or surrounding tissue, such as arteries, arterioles, capillaries, veins or venules. In some embodiments, the treatment may be achieved via direct application of energy to the target or support structures. In other embodiments, the treatment may be achieved via indirect generation and/or application of the energy, such as through application of an electric field or of high-intensity focused ultrasound that causes resistive heating in the target or supporting structures. Alternative thermal techniques also may be utilized.

In some embodiments, methods and apparatus for real-time monitoring of the treatment and its effects on the target or support structures, and/or in non-target tissue, may be provided. Likewise, real-time monitoring of the energy delivery apparatus may be provided. Power or total energy delivered, impedance and/or the temperature, or other characteristics of the target or non-target tissue, or of the apparatus, additionally or alternatively may be monitored.

When utilizing an electric field to achieve desired circumferential treatment, the electric field parameters may be altered and combined in any combination, as desired. Such parameters can include, but are not limited to, frequency, voltage, power, field strength, pulse width, pulse duration, the shape of the pulse, the number of pulses and/or the interval between pulses (e.g., duty cycle), etc. For example, suitable field strengths can be up to about 10,000 V/cm, and may be either continuous or pulsed. Suitable shapes of the electrical waveform include, for example, AC waveforms, sinusoidal waves, cosine waves, combinations of sine and cosine waves, DC waveforms, DC-shifted AC waveforms, RF waveforms, microwaves, ultrasound, square waves, trapezoidal waves, exponentially-decaying waves, and combinations thereof.

When utilizing a pulsed electric field, suitable pulse widths can be of any desired interval, for example, up to about 1 second. The field includes at least one pulse, and in many applications the field includes a plurality of pulses or is continuously applied, e.g., for up to several minutes. Suitable pulse intervals include, for example, intervals less than about 10 seconds. These parameters are provided as suitable examples and in no way should be considered limiting.

When utilizing thermal mechanisms to achieve the desired treatment, protective elements optionally may be provided to protect the non-target tissue, such as the smooth muscle cells, from thermal damage during the thermally-induced non-continuous circumferential treatment. For example, when heating target nerves or support structures, protective cooling elements, such as convective cooling elements, may be provided to protect the non-target tissue. Likewise, when cooling target nerves or support structures, protective heating elements, such as convective heating elements, may be utilized to protect the non-target tissue. Thermal energy may be applied either directly or indirectly for a brief or a sustained period of time in order to achieve, for example, desired neuromodulation or denervation. Feedback, such as sensed temperature and/or impedance, along target or non-target tissue or along the apparatus, optionally may be used to control and monitor delivery of the thermal energy.

The non-target tissue optionally may be protected during, e.g., the neuromodulation or denervation, by utilizing blood flow as a conductive and/or convective thermal sink that absorbs excess thermal energy (hot or cold). For example, when blood flow is not blocked, the circulating blood may provide a relatively constant temperature medium for removing the excess thermal energy from the non-target tissue during the procedure. The non-target tissue additionally or alternatively may be protected by focusing the thermal (or other) energy on the target or support structures, such that an intensity of the energy is insufficient to induce thermal damage in the non-target tissue distant from the target or support structures.

Additional and alternative methods and apparatus may be utilized to achieve a non-continuous circumferential treatment without formation of a continuous circumferential lesion, as described hereinafter. To better understand the structures of devices of the present invention and the methods of using such devices for non-continuous circumferential treatment, it is instructive to examine a common neurovascular anatomy in humans.

B. Neurovascular Anatomy Summary

FIG. 1 illustrates a common anatomical arrangement of neural structures relative to body lumens or vascular structures, typically arteries. Neural fibers N generally may extend longitudinally along the lengthwise dimension L of an artery A about a relatively small range of positions along the radial dimension r, often within the adventitia of the artery. The artery A has smooth muscle cells SMC that surround the arterial circumference and generally spiral around the angular dimension θ of the artery, also within a relatively small range of positions along the radial dimension r. The smooth muscle cells of the artery accordingly have a lengthwise or longer dimension generally extending transverse (i.e., non-parallel) to the lengthwise dimension of the blood vessel. The misalignment of the lengthwise dimensions of the neural fibers and the smooth muscle cells is defined as "cellular misalignment."

The cellular misalignment of the nerves N and the smooth muscle cells SMC may be exploited to selectively affect the nerve cells with reduced effect on the smooth muscle cells. More specifically, a non-continuous circumferential treatment may be achieved by superimposing treatments undertaken along multiple radial or cross-sectional planes of the artery A that are separated along the lengthwise dimension L of the artery, rather than performing a continuous circumferential treatment along a single radial plane or cross-section of the artery. In this manner, due to the cellular misalignment, the lengthwise-oriented neural fibers may experience a full, non-continuous circumferential treatment, while the angularly-oriented smooth muscle cells may experience only a partial circumferential treatment. Monitoring elements optionally may be utilized to assess an extent of treatment induced in the nerves and/or in the smooth muscle cells, as well as to adjust treatment parameters to achieve a desired effect.

C. Embodiments of Apparatus and Methods for Non-continuous Circumferential Treatment of a Body Lumen FIGS. 2-7 and 9 illustrate examples of intravascular systems and methods for performing non-continuous circumferential treatments. The applicants have described intravascular and intra-to-extravascular systems for neuromodulation or denervation, for example, in Applicants' U.S. Pat. Nos. 7,653,438 and 7,620,451, both of which have been incorporated herein by reference. The applicants also have described extravascular systems for neuromodulation or denervation (see, for example, U.S. Pat. No. 8,145,316, incorporated herein by reference), and it should be understood that non-continuous circumferential treatments may be performed using extravascular (or extraluminal) systems, in addition to intravascular (intraluminal) or intra-to-extravascular (intra-to-extraluminal) systems (see FIGS. 10A and 10B). Applicants also have previously described thermal systems for neuromodulation or denervation, for example, in Applicants' U.S. Pat. No. 7,617,665.

Referring now to FIGS. 2A-2J, the embodiment of an apparatus 300 comprises a catheter 302 having an optional positioning element 304 (e.g., a balloon, an expandable wire basket, other mechanical expanders, etc.) and expandable electrode element 306 positioned along the shaft of the catheter and illustratively located over the positioning element. The electrode element 306 can have one or more electrodes 307 electrically coupled to a field generator 50 for delivery of an electric field to the target neural fibers. In an alternative embodiment, one or more of the electrode(s) 307 of the electrode element 306 may comprise Peltier electrodes for heating or cooling the target neural fibers to modulate the fibers. The electrode(s) 307 optionally may be individually assignable and may be utilized in a bipolar fashion, and/or may be utilized in a monopolar fashion with an external ground pad attached to the exterior of the patient.

The field generator 50, as well as any of the electrode embodiments described herein, may be utilized with any embodiment of the present invention for delivery of an electric field with desired field parameters. The field generator 50 can be external to the patient. It should be understood that electrodes of embodiments described hereinafter may be electrically connected to the generator even though the generator is not explicitly shown or described with each embodiment. Furthermore, the field generator optionally may be positioned internal to the patient, and the electrodes and/or the field generator optionally may be temporarily or permanently implanted within the patient.

The positioning element 304 optionally may position or otherwise drive the electrode(s) 307 into contact with the vessel wall. The positioning element 304 may also comprise an impedance-altering element that alters the impedance within the vessel during the therapy to direct the electric field across the vessel wall. This may reduce an energy required to achieve desired neuromodulation or denervation and may reduce a risk of injury to non-target tissue. Applicants have previously described use of an impedance-altering element, for example, in Applicants' U.S. Pat. No. 7,756,583, which is incorporated herein by reference in its entirety. When the positioning element 304 comprises an inflatable balloon, as in FIGS. 2A-J, the balloon may serve as both a centering and/or expansion element for the expandable electrode element 306, and as an impedance-altering electrical insulator for directing an electric field delivered via the electrode(s) 307 into or across the vessel wall for modulation of target neural fibers. Electrical insulation provided by the element 304 may reduce the magnitude of applied energy or other parameters of the electric field necessary to achieve desired modulation of the target fibers, up to and including full denervation of tissue containing the target fibers.

Furthermore, element 304 optionally may be utilized as a thermal element. For example, it may be inflated with a chilled fluid that serves as a heat sink for removing heat from tissue that contacts the element. Conversely, element 304 may be inflated with a warmed fluid that heats tissue in contact with the element. The thermal fluid within the element optionally may be circulated and/or exchanged within the positioning element 304 to facilitate more efficient conductive and/or convective heat transfer. Thermal fluids also may be used to achieve thermal neuromodulation via thermal cooling or heating mechanisms, as described in greater detail herein below.

The electrode(s) 307 can be individual electrodes (i.e., independent contacts), a segmented electrode with commonly connected contacts, or a single continuous electrode. Furthermore, the electrode(s) 307 may be configured to provide a bipolar signal, or the electrode(s) 307 may be used together or individually in conjunction with a separate patient ground pad for monopolar use. As an alternative or in addition to placement of the electrode(s) 307 along the expandable electrode element 306, as in FIG. 2, the electrode(s) 307 may be attached to the positioning element 304 such that they contact the wall of the artery upon expansion of the positioning element. In such a variation, the electrode(s) may, for example, be affixed to the inside surface, outside surface or at least partially embedded within the wall of the positioning element (see FIGS. 5A and 5B). In another embodiment, the electrode(s) do not contact the vessel wall, and may be positioned at any desired location within the vessel.

The electrode(s) 307 or any other portion of the apparatus 300, such as catheter 302 or element 304, additionally or alternatively may comprise one or more sensors, such as thermocouples 310, for monitoring the temperature or other parameters of the target tissue, the non-target tissue, the electrodes, the positioning element and/or any other portion of the apparatus 300 or of the patient's anatomy. The treatment regime may be controlled using the measured parameter(s) as feedback. This feedback may be used, for example, to maintain the parameter(s) below a desired threshold, for example, a threshold that may cause injury to the non-target tissues. Conversely, the feedback may be used to maintain the parameter(s) at or above a desired threshold, for example, a threshold that may induce a desired effect in the target tissues, such as neuromodulation of target neural fibers or denervation of tissues innervated by the target neural fibers. Furthermore, the feedback may be used to keep the parameter(s) within a range that will induce the desired effect in the target tissues without injuring the non-target tissues to an unacceptable extent. Multiple parameters (or the same or multiple parameters at multiple locations) optionally may be used as control feedback for ensuring the desired effects while mitigating the undesired effects while mitigating the undesired effects.

Figure 2A:
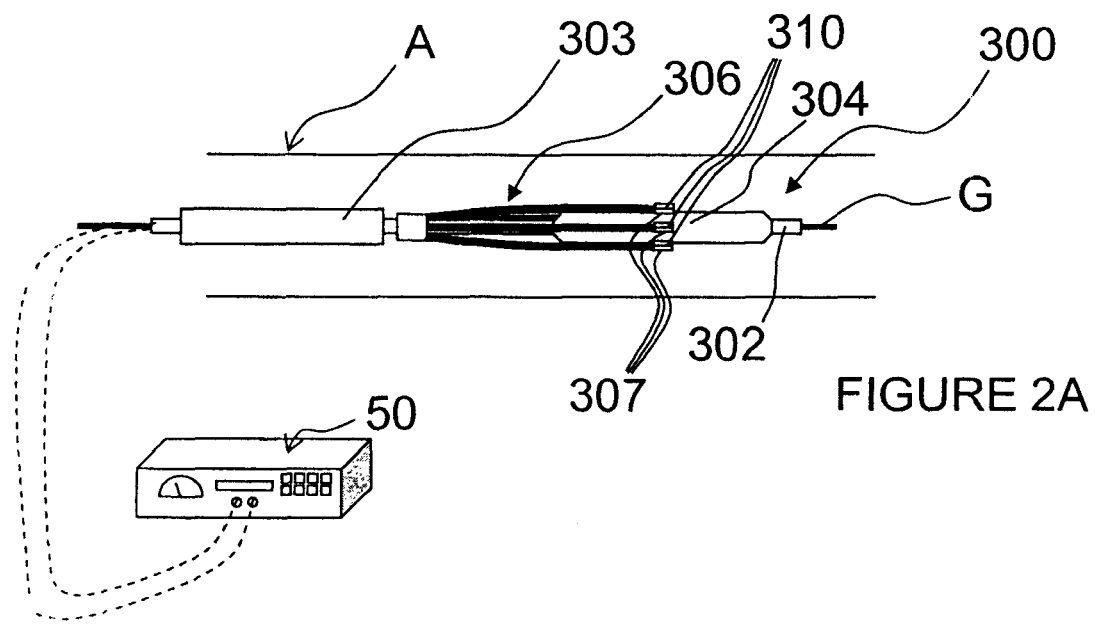
FIGS. 2A-2J are schematic side views, partially in section, and cross-sectional views illustrating an example of methods and apparatus for a non-continuous circumferential treatment of a body lumen.

As seen in FIG. 2A, the catheter 302 may be delivered to a treatment site within the artery A (or within a vein or any other vessel in proximity to target neural fibers) in a low profile delivery configuration, for example, through the guide catheter or sheath 303. Alternatively, catheters may be positioned in multiple vessels for neuromodulation, e.g., within both an artery and a vein. Multi-vessel techniques for electric field neuromodulation have been described previously, for example, in Applicant's U.S. Pat. No. 7,853,333, which is incorporated herein by reference in its entirety.

Figure 2B:
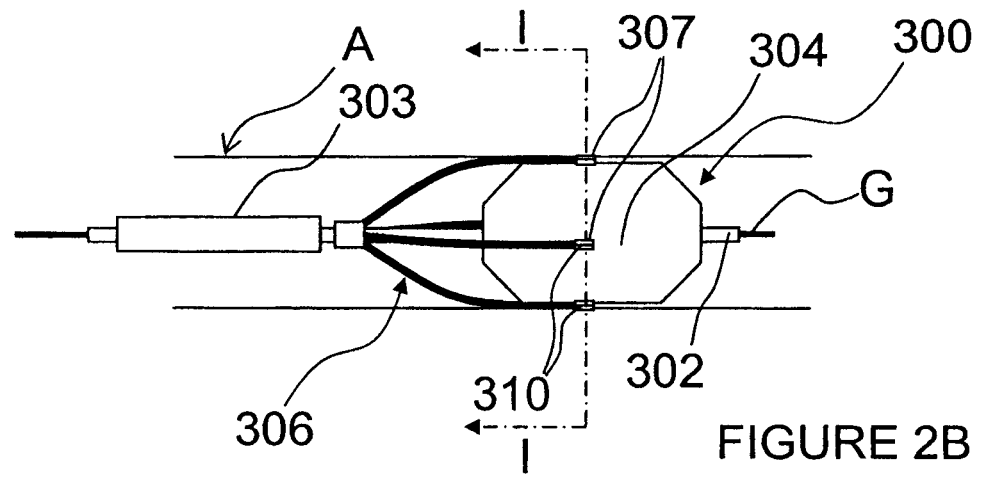

Once positioned within the vasculature as desired, the optional positioning element 304 may be expanded to display the electrode element 306 and bring the electrode(s) 307 into contact with an interior wall of the vessel, as seen in FIG. 2B. An electric field then may be generated by the field generator 50, transferred through the catheter 302 to the electrode element 306 and the electrodes 307, and delivered via the electrode(s) 307 across the wall of the artery. The electric field modulates the activity along neural fibers within the wall of the artery or in proximity to the artery, e.g., at least partially denervates tissue or organ(s) innervated by the neural fibers. This may be achieved, for example, via ablation or necrosis or via non-ablative injury or other changes to the target neural fibers or supporting structures. The electric field also may induce electroporation in the neural fibers.

Figure 2C:
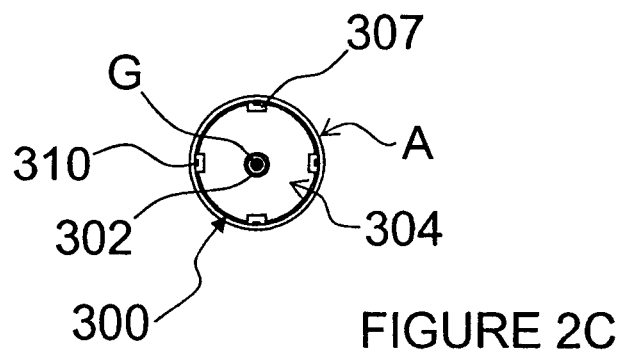
Figure 2D:
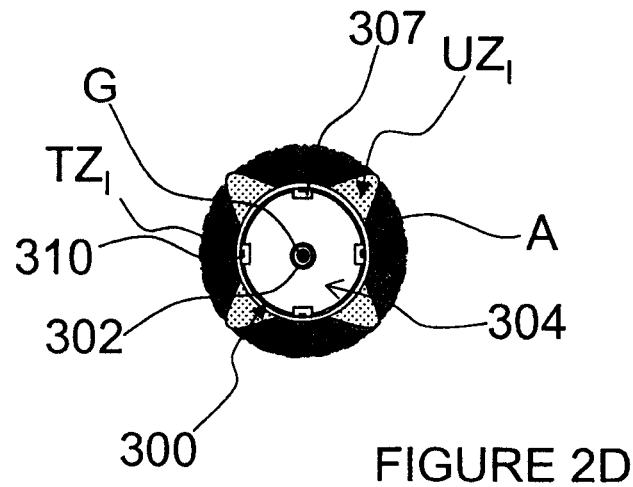

As seen in the cross-sectional view of FIG. 2C taken along the radial plane I-I of FIG. 2B, the apparatus 300 illustratively comprises four electrodes 307 equally spaced about the circumference of the electrode element 306 and the positioning element 304. As seen in FIG. 2D, when utilized in a monopolar fashion in combination with an external ground (not shown; per se known), the circumferential segments treated by each electrode overlap to form discrete treatment zones $TZ_I$ that are not continuous completely around the circumference of the artery in a radial plane normal to the vessel wall. As a result, there are discrete untreated zones $UZ_I$ about the circumference of the artery.

Figure 2E:
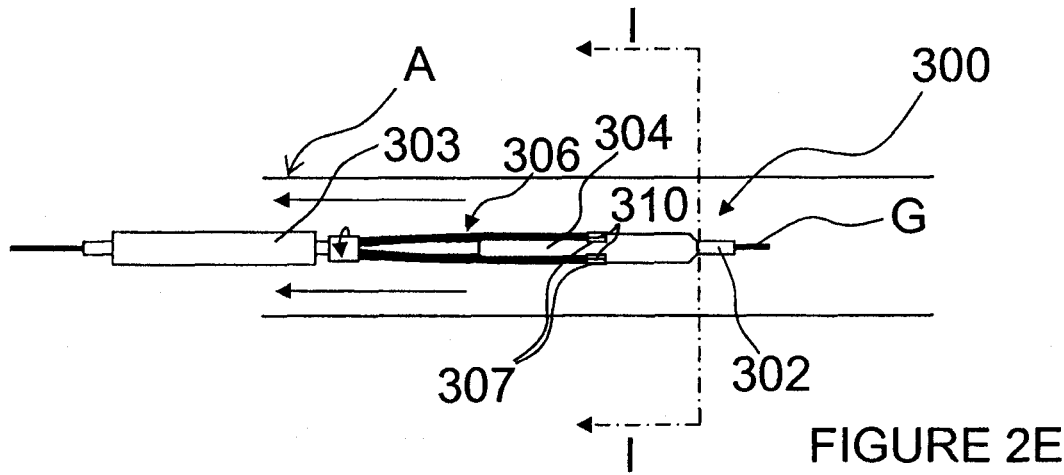

As seen in FIG. 2E, the electrode element 306 may be collapsed about the radial dimension r of the artery such that the electrodes 307 do not contact the vessel wall, e.g., by collapsing the positioning element 304. The electrode element 306 may be rotated about the angular dimension θ of the artery to angularly reposition the electrodes 307 (best shown in FIG. 2G). This rotation may be achieved, for example, by angularly rotating the catheter 302. In FIG. 2E, the electrode element illustratively has been rotated approximately 45° about the angular dimension of the artery. In the embodiment of apparatus 300 shown in FIGS. 2A-G, the electrodes are equally spaced about the circumference of the apparatus such that a 45° angular rotation repositions the electrodes approximately halfway between the initial positions of the electrodes shown in FIG. 2D.

Figure 2F:
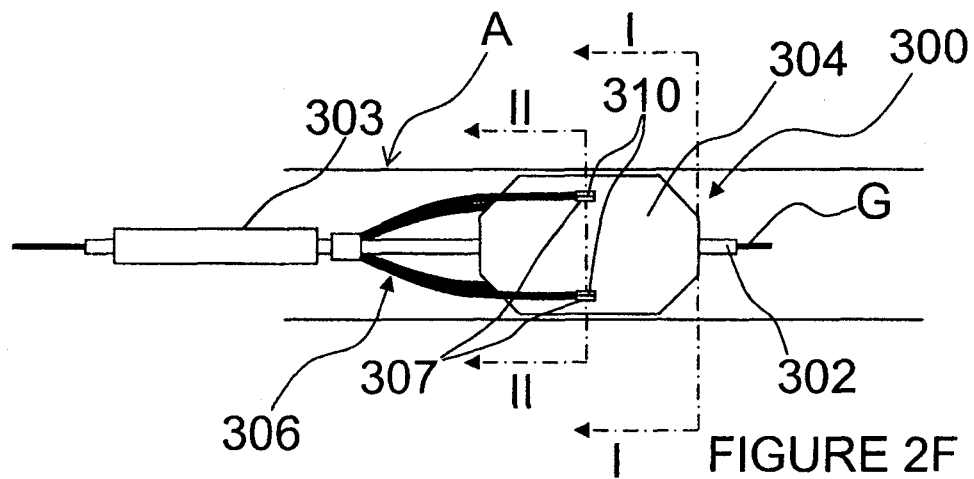

In addition to angular repositioning of the electrodes, the electrodes may be repositioned along the lengthwise or longitudinal dimension L of the artery, which is also shown in FIG. 2E as the longitudinal offset between the electrodes 307 and the radial plane I-I. Such lengthwise repositioning may occur before, after or concurrent with angular repositioning of the electrodes. As seen in FIG. 2F, once repositioned in both the lengthwise and angular dimensions, the electrode element 306 may be re-expanded about the radial dimension to contact the electrodes 307 with the vessel wall. An electric field then may be delivered via the angularly and lengthwise repositioned electrodes 307 along the normal radial plane II-II.

Figure 2G:
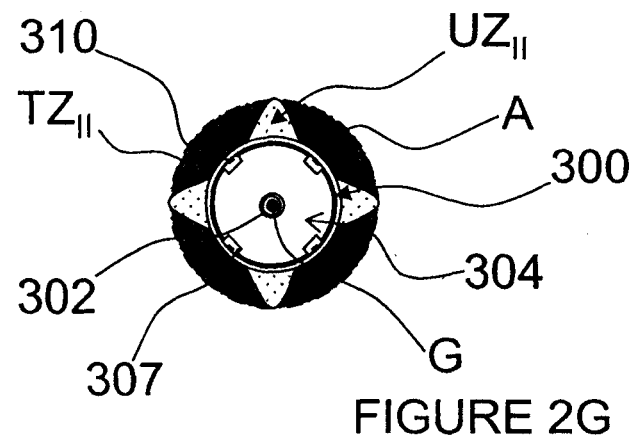
Figures 2H, 2I:
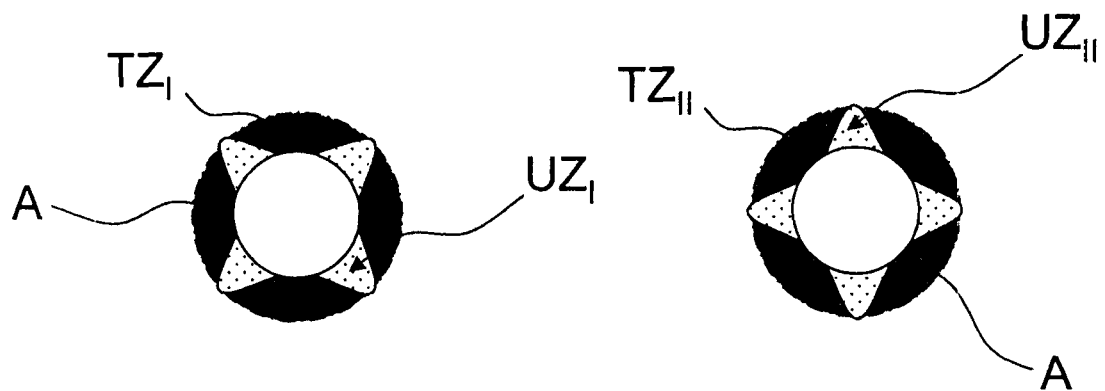

In FIG. 2G, the treatment along radial plane II-II of FIG. 2F creates treatment zone $TZ_{II}$ and untreated zone $UZ_{II}$. As with the treatment zone $TZ_I$ of FIG. 2D, the treatment zone $TZ_{II}$ of FIG. 2G is not continuous about the complete circumference of the artery. FIGS. 2H and 2I allow comparison of the treatment zone $TZ_I$ and the treatment zone $TZ_{II}$. The apparatus 300 is not shown in FIGS. 2H and 2I, e.g., the apparatus may have been removed from the patient to complete the procedure.

Figure 2J:
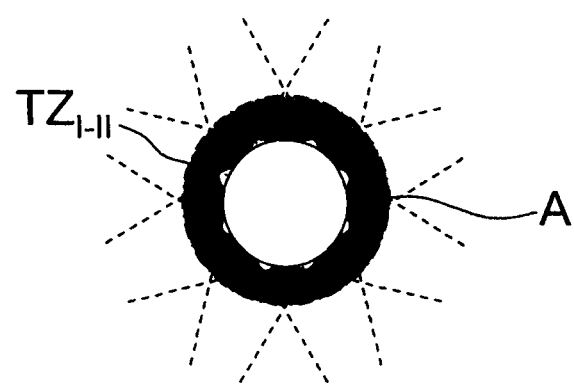

As shown, the untreated zones $UZ_I$ and $UZ_{II}$ along the radial planes I-I and II-II, respectively, are angularly offset from one another about the angular dimension θ of the artery (see FIG. 1). As seen in FIG. 2J, by superimposing the treatment zones $TZ_I$ and $TZ_{II}$, which are positioned along different cross-sections or radial planes of the artery A, a composite treatment zone $TZ_{I-II}$ is formed that provides a non-continuous, yet substantially circumferential treatment over a lengthwise segment of the artery. This superimposed treatment zone beneficially does not create a continuous circumferential lesion along any individual radial plane or cross-section normal to the artery, which may reduce a risk of acute or late stenosis formation, as compared to previous circumferential treatments that create a continuous circumferential lesion.

As discussed previously, non-continuous circumferential treatment by positioning electrodes at different angular orientations along multiple lengthwise locations may preferentially affect anatomical structures that substantially propagate along the lengthwise dimension of the artery. Such anatomical structures can be neural fibers and/or structures that support the neural fibers. Furthermore, such a non-continuous circumferential treatment may mitigate or reduce potentially undesirable effects induced in structures that propagate about the angular dimension of the artery, such as smooth muscle cells. The angular or circumferential orientation of the smooth muscle cells relative to the artery may at least partially explain why continuous circumferential lesions may increase a risk of acute or late stenosis.

Although in FIGS. 2A-J the electrode element 306 is expanded via the positioning element 304, it should be understood that expandable electrode elements or electrodes in accordance with the present invention additionally or alternatively may be configured to self-expand into contact with the vessel wall. For example, the electrodes may self-expand after removal of a sheath or a guide catheter 303 constraining the electrodes in a reduced delivery configuration. The electrodes or electrode elements may, for example, be fabricated from (or coupled to) shape-memory elements that are configured to self-expand. Self-expanding embodiments optionally may be collapsed for retrieval from the patient by re-positioning of a constraining sheath or catheter over the self-expanding elements. Optionally, the electrode element may be shapeable by a medical practitioner, e.g., in order to provide a desired wall-contacting profile.

Figure 3:
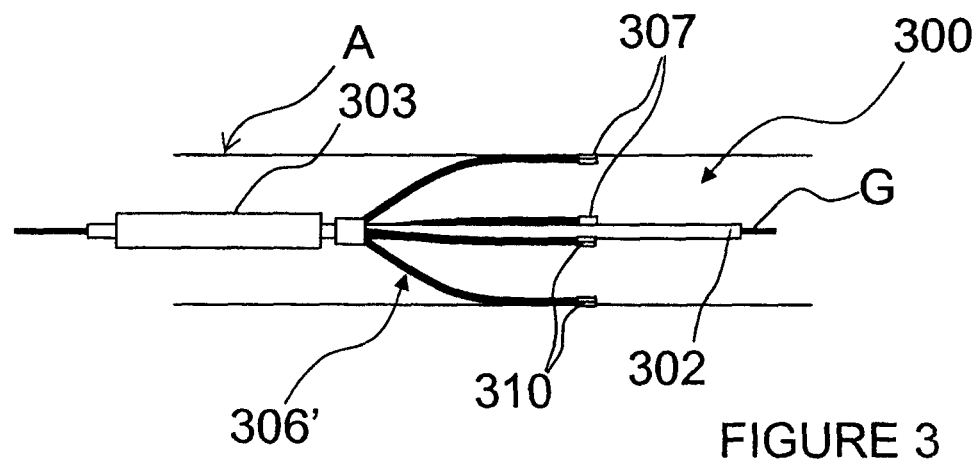
FIG. 3 is a schematic side view, partially in section, illustrating an alternative embodiment of the methods and apparatus of FIG. 2.

FIG. 3 illustrates an alternative embodiment of the apparatus 300 having a self-expanding electrode element 306'. Positioning element 304 has been removed from the apparatus. In use, the apparatus 300 is advanced to a treatment site within sheath or guide catheter 303. The sheath is removed, and the element 306' self-expands to bring the electrodes 307 into contact with the vessel wall. Advantageously, blood continues to flow through the artery A during formation of treatment zone $TZ_I$. The element 306' then may be partially or completely collapsed (e.g., within sheath 303), angularly rotated relative to the vessel, laterally repositioned relative to the vessel, and re-expanded into contact with the vessel wall along a different radial plane or cross-section. Treatment may proceed at the new location and in the new angularly orientation in the presence of blood flow, e.g., to form overlapping treatment zone $TZ_{II}$ that completes a non-continuous circumferential treatment zone when superimposed with the treatment zone $TZ_I$. The element 306' then may be re-collapsed, and the apparatus 300 may be removed from the patient to complete the procedure.

Figure 4:
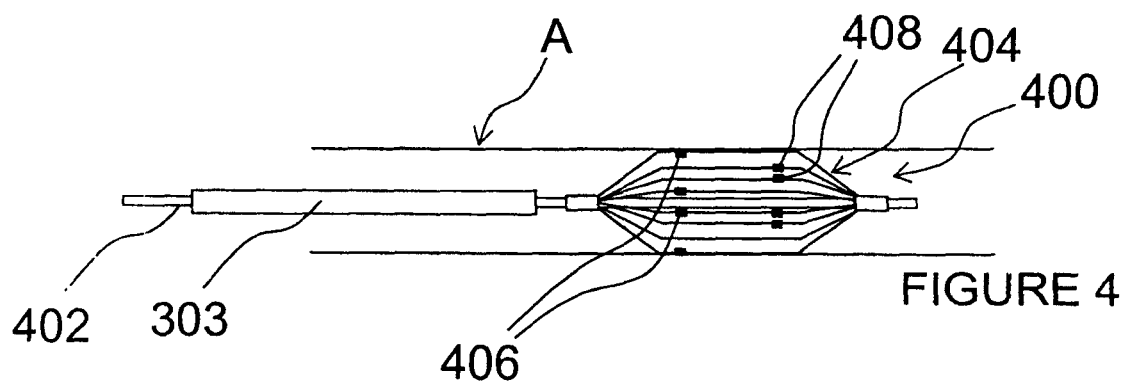
FIG. 4 is a schematic side view, partially in section, illustrating further alternative methods and apparatus for non-continuous circumferential treatments.

Referring now to FIG. 4, it may be desirable to achieve a non-continuous circumferential treatment without angular and/or lengthwise repositioning of electrodes or other energy delivery elements. To this end, in another embodiment an apparatus 400 comprises catheter 402 having actively-expandable or self-expanding basket 404 having proximal electrodes 406 and distal electrodes 408 spaced longitudinally apart from the proximal electrodes. The proximal electrodes 406 and distal electrodes 408 are also spaced apart radially about the basket and electrically coupled to the field generator 50 (see FIG. 2A). The proximal electrodes 406 can be positioned along different struts or elements of the basket than the distal electrodes. The proximal and distal electrodes are accordingly angularly and laterally offset from one another.

The proximal electrodes may be operated independently of the distal electrodes, and/or the proximal and distal electrodes all may be operated at the same polarity, e.g., in a monopolar fashion as active electrodes in combination with an external ground. Alternatively or additionally, the proximal electrodes may be utilized in a bipolar fashion with one another and/or the distal electrodes may be utilized in a bipolar fashion with one another. The proximal and distal electrodes preferably are not utilized together in a bipolar fashion. By treating with the distal electrodes 408, the treatment zone $TZ_I$ of FIG. 2H may be formed about the artery. Treating with the proximal electrodes 406 may create the treatment zone $TZ_{II}$ of FIG. 2I, which is angularly offset relative to the treatment zone $TZ_I$. Superimposition of the treatment zones $TZ_I$ and $TZ_{II}$ creates the non-continuous circumferential treatment zone $TZ_{I-II}$ over a lengthwise segment of the artery.

The proximal and distal electrodes optionally may be utilized concurrently to concurrently form the treatment zones $TZ_I$ and $TZ_{II}$. Alternatively, the electrodes may be operated sequentially in any desired order to sequentially form the treatment zones. As yet another alternative, the treatment zones may be formed partially via concurrent treatment and partially via sequential treatment.

Figure 5A:
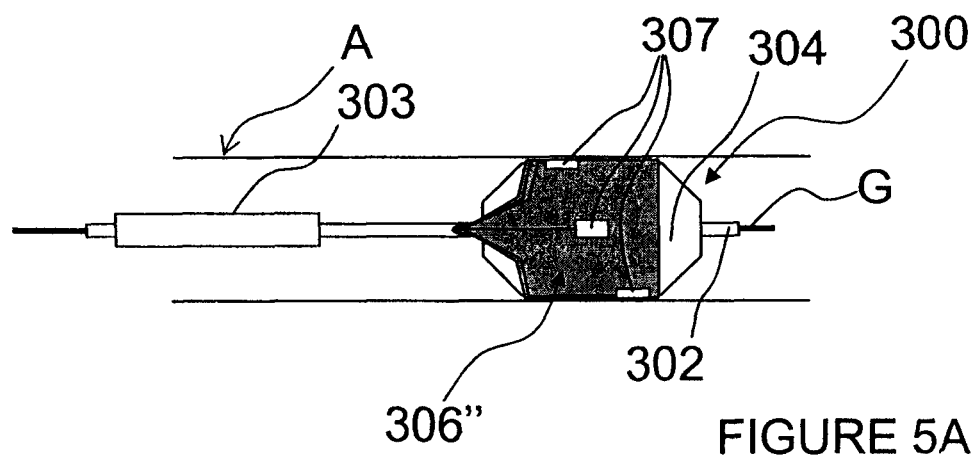
FIGS. 5A and 5B are schematic side views, partially in section, illustrating still further alternative methods and apparatus for non-continuous circumferential treatments.
Figure 5B:
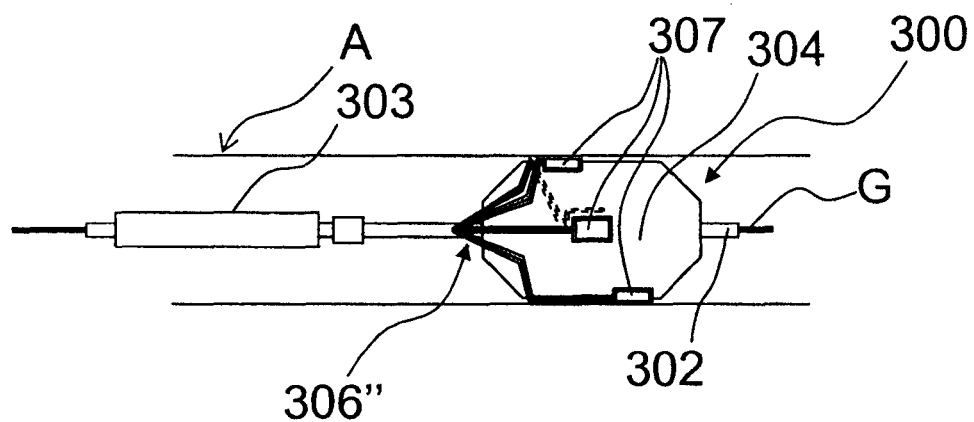

FIGS. 5A and 5B describe additional apparatus and methods for non-continuous circumferential treatment without having to reposition electrodes or other energy delivery elements. As seen in FIGS. 5A and 5B, the apparatus 300 has an electrode element 306" that comprises a flex circuit coupled to or positioned about the positioning element 304. The flex circuit is electrically coupled to the field generator 50 by wires that extend through or along the catheter 302 or by wireless. In FIG. 5A, the flex circuit comprises a collapsible cylinder positioned about the positioning element 304. In FIG. 5B, the flex circuit comprises individual electrical connections for each electrode 307, which may facilitate collapse of the flex circuit for delivery and retrieval. As with the electrodes of apparatus 400 of FIG. 4, the electrodes 307 of FIG. 7 are spaced at multiple lengthwise positions relative to the positioning element and the blood vessel. The electrodes may be operated as described previously to achieve a non-continuous circumferential treatment. As the electrodes 307 illustratively are positioned at three different lengthwise positions, the non-continuous circumferential treatment may, for example, be formed via superimposition of three treatment zones (one at each lengthwise position within the blood vessel).

With any of the embodiments described herein, during delivery of the electric field (or of other energy), blood within the vessel may act as a thermal sink (either hot or cold) for conductive and/or convective heat transfer for removing excess thermal energy from the non-target tissue (such as the interior wall of the vessel), thereby protecting the non-target tissue. This effect may be enhanced when blood flow is not blocked during energy delivery, for example, as in the embodiments of FIGS. 3 and 4 (it should be understood that a variation of the embodiments of FIG. 5 may provide for blood flow; for example, the electrode(s) may be brought into contact with the vessel wall via an expandable basket rather than via an inflatable balloon). Use of the patient's blood as a thermal sink is expected to facilitate delivery of longer or higher energy treatments with reduced risk of damage to the non-target tissue, which may enhance the efficacy of the treatment at the target tissue, for example, at target neural fibers.

In addition or as an alternative to utilizing the patient's blood as a thermal sink, a thermal fluid (hot or cold) may be injected, infused or otherwise delivered into the vessel to remove excess thermal energy and protect the non-target tissues. This method of using an injected thermal fluid to remove excess thermal energy from non-target tissues to protect the non-target tissues from thermal injury during therapeutic treatment of target tissues may be utilized in body lumens other than blood vessels. The thermal fluid may, for example, comprise chilled or room temperature saline (e.g., saline at a temperature lower than the temperature of the vessel wall during the therapy delivery). The thermal fluid may, for example, be injected through the device catheter or through a guide catheter. The thermal fluid injection may be in the presence of blood flow or with flow temporarily occluded. Occlusion of flow in combination with thermal fluid delivery may facilitate better control over the heat transfer kinetics along the non-target tissues, as well as optional injection of the fluid from a downstream location.

Figure 6A:
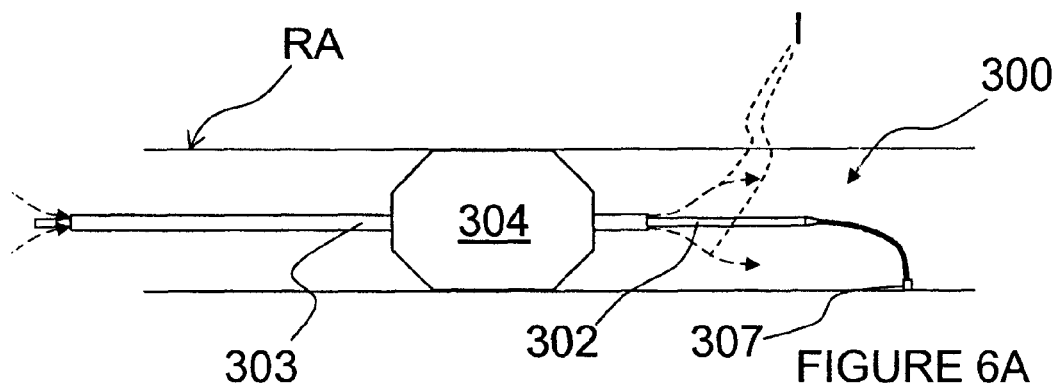
FIGS. 6A and 6B are schematic side views, partially in section, illustrating additional alternative methods and apparatus for non-continuous circumferential treatments.

Referring now to FIG. 6, another embodiment of the apparatus 300 is described that comprises optional flow occlusion and thermal fluid injection. The optional occlusion/positioning element 304 illustratively is coupled to the guide catheter 303, and the catheter 302 may be repositioned relative to the guide catheter to reposition the electrode(s) 307, optionally without re-establishing flow through the vessel. In FIG. 6, the alternative electrode element 306''' is self-expanding, and/or is shapeable (e.g., is formed from a spring steel) by a medical practitioner to provide a desired profile for positioning of the electrode(s) 307 into contact with the vessel wall.

The catheter 302 may be advanced within the renal artery RA in a reduced profile delivery configuration. Once properly positioned, the electrode element 306''' may self-expand (or may be actively expanded) to bring the electrode(s) 307 into contact with the vessel wall, for example, by removing the electrode element from the lumen of the guide catheter. The element 304 also may be expanded (before, during or after expansion of the electrode element) in order to properly position the electrode within the vessel and/or to occlude blood flow within, e.g., the renal artery. An electric field, such as a monopolar electric field, may be delivered via the electrode(s) 307, e.g., between the electrode(s) and an external ground (not shown; per se known). The electric field may, for example, comprise a pulsed or continuous RF electric field that thermally induces neuromodulation (e.g., necrosis or ablation) in the target neural fibers. The therapy may be monitored and/or controlled, for example, via data collected with thermocouples or other sensors, e.g., impedance sensors.

In order to increase the power or duration of the treatment that may be delivered without damaging non-target tissue of the vessel wall to an unacceptable extent, a thermal fluid infusate I may be injected, e.g., through the guide catheter 303 to cool (heat) the non-target tissue, thereby mitigating damage to the non target tissue. The infusate may, for example, comprise chilled saline that removes excess thermal energy (hot or cold) from the wall of the vessel during thermal RF therapy.

Convective or other heat transfer between the non-target vessel wall tissue and the infusate I may facilitate cooling (heating) of the vessel wall at a faster rate than cooling (heating) occurs at the target neural fibers. This heat transfer rate discrepancy between the wall of the vessel and the target neural fibers may be utilized to modulate the neural fibers with reduced damage to the vessel wall. Furthermore, when utilizing a pulsed therapy, the accelerated heat transfer at the wall relative to the neural fibers may allow for relatively higher power or longer duration therapies (as compared to continuous therapies), due to the additional time between pulses for protective cooling at the vessel wall. Also, the interval between pulses may be used to monitor and/or control effects of the therapy.

Figure 6B:
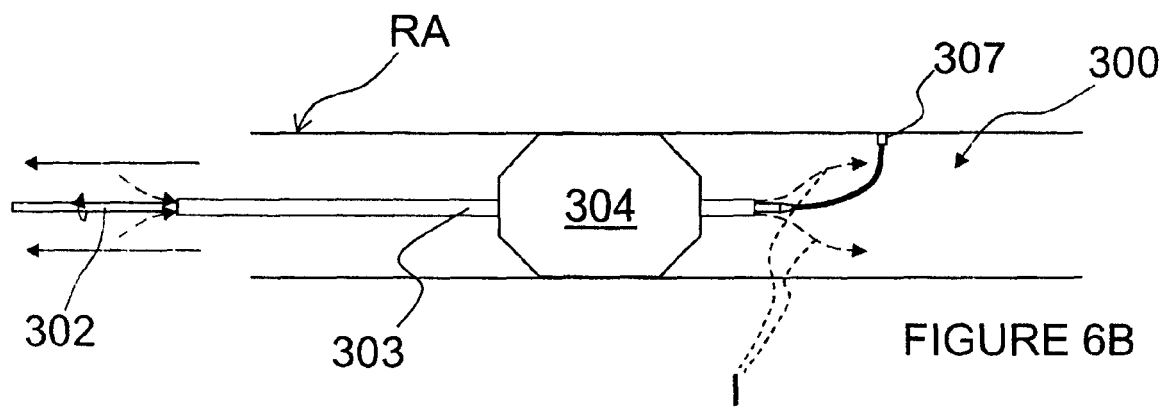

Referring now to FIG. 6B, treatment at additional angular and lengthwise positions relative to the vessel wall may be achieved by rotation and lengthwise repositioning of the catheter 302. This may be repeated at as many lengthwise and/or angular positions as desired by the medical practitioner. The treatment(s) at each individual lengthwise position preferably do not form a continuous circumferential lesion normal to the vessel wall, while superimposition of the treatments at multiple such lengthwise positions preferably forms a non-continuous, partially or fully circumferential lesion, as described previously.

Figure 7A:
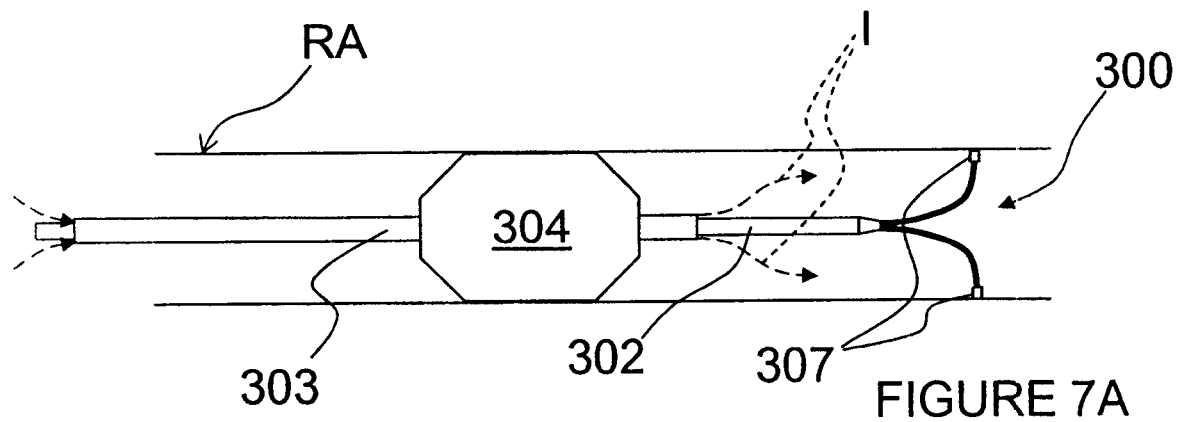
FIGS. 7A and 7B are schematic side views, partially in section, illustrating alternative embodiments of the apparatus and methods of FIG. 6.
Figure 7B:
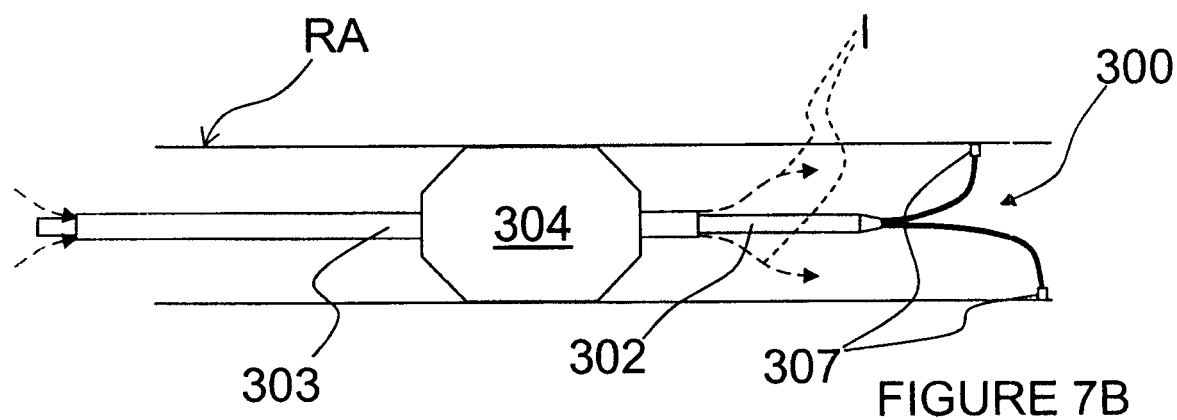

In the embodiment of the FIG. 6, the apparatus illustratively comprises a single electrode 307. However, multiple such electrodes optionally may be provided at multiple, angularly-offset positions, as in FIG. 7A. This may reduce the number of lengthwise positions where treatment needs to be conducted in order to achieve the non-continuous, substantially circumferential treatment of the present invention. In addition or as an alternative to angular offsetting, the electrodes optionally may be offset lengthwise from one another, such that treatment at the multiple lengthwise positions may be achieved concurrently or sequentially without necessitating lengthwise repositioning of the electrodes. FIG. 7B illustrates an embodiment of apparatus 300 having multiple electrodes that are offset from one another both angularly and lengthwise. In such an embodiment, the relative angular and lengthwise positions of the electrodes may be fixed or may be dynamically alterable by the medical practitioner.

Figure 8:
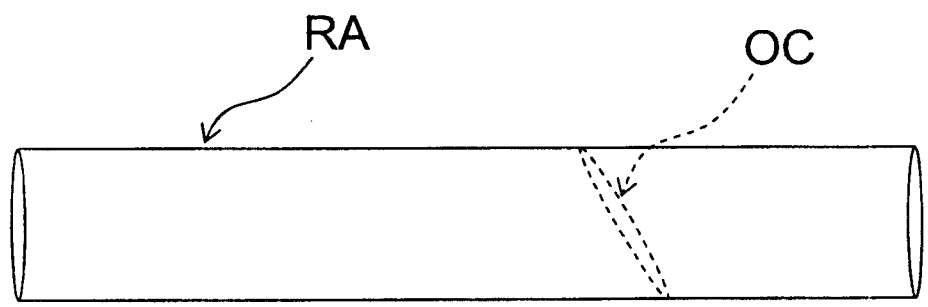
FIG. 8 is a schematic side view, illustrating a non-continuous circumferential treatment that is oblique to the lengthwise axis of the patient's vasculature.

As described herein, a continuous circumferential lesion is a circumferential lesion that is substantially continuous in a radial plane normal to the vessel or luminal wall. Conversely, a non-continuous circumferential lesion may be non-continuous relative to a normal radial plane, but substantially continuous along an oblique plane of the vasculature that is not normal to the vessel wall. For example, as seen in dotted profile in FIG. 8, an oblique circumferential treatment OC may be achieved within the patient's vasculature, e.g., the patient's renal artery RA, without formation of a continuous circumferential treatment relative to a normal radial plane of the vasculature. The previously-described apparatus and methods of FIG. 5 may, for example, form such an oblique circumferential treatment OC.

Figure 9A:
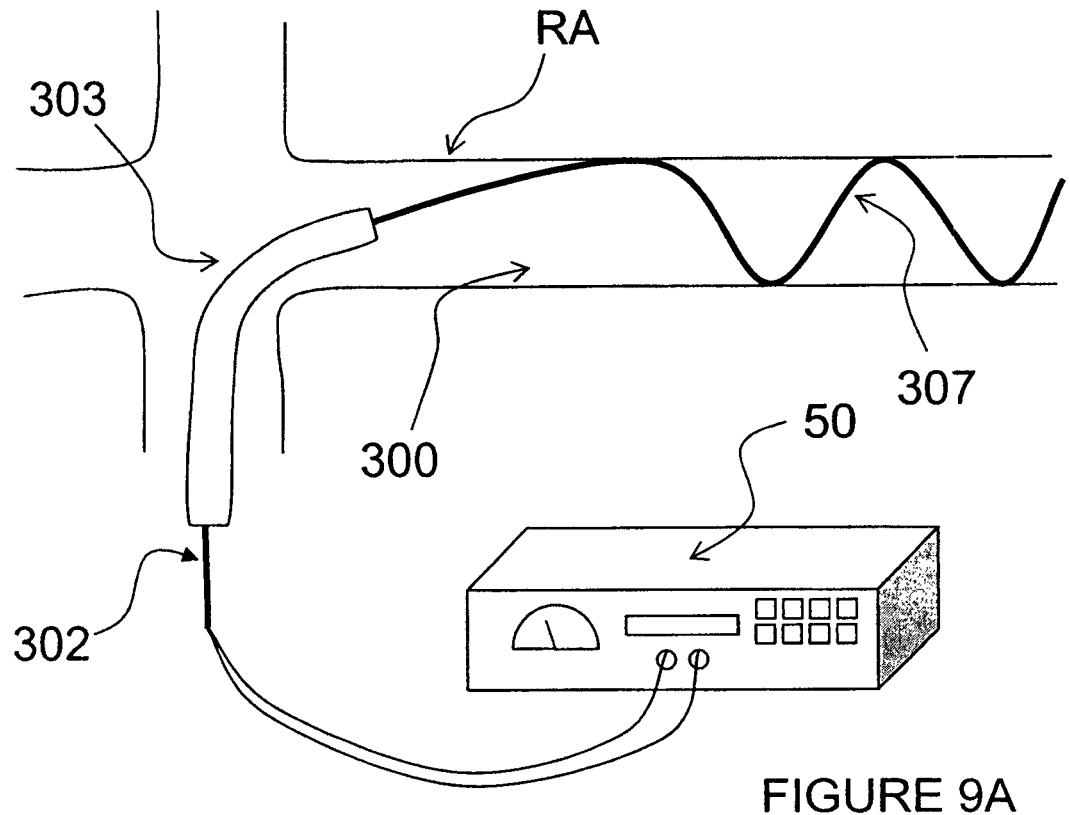
FIGS. 9A and 9B are schematic side views, partially in section, illustrating intravascular methods and apparatus for oblique circumferential treatment.
Figure 9B:
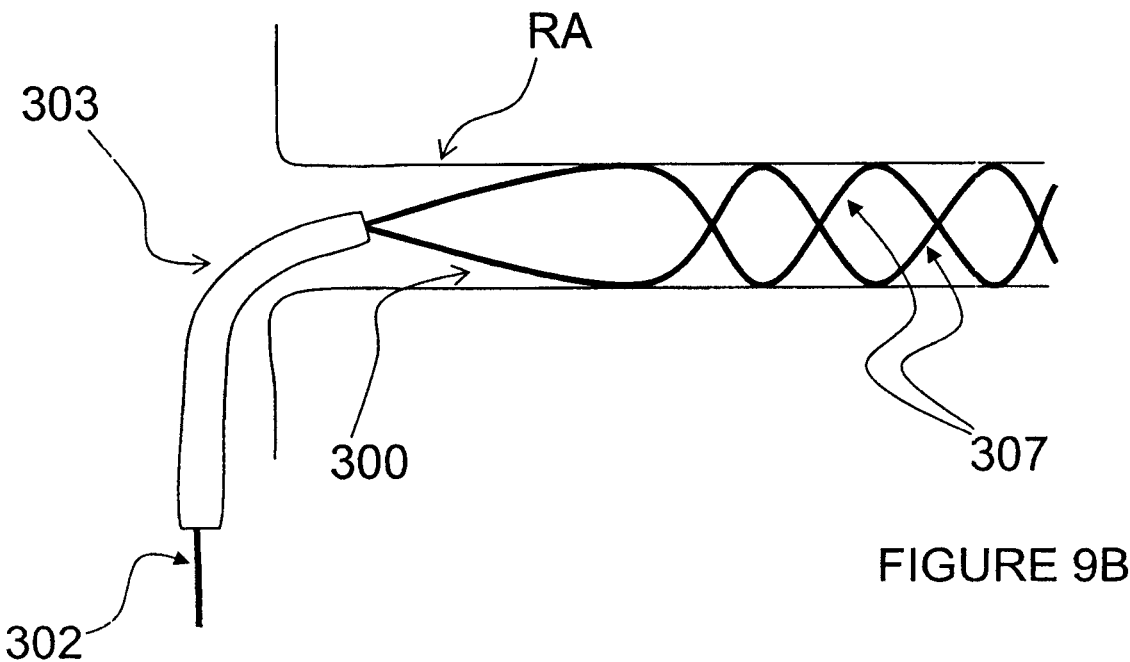

FIGS. 9A and 9B illustrate additional methods and apparatus for achieving such oblique circumferential treatments. In FIG. 9A, the apparatus 300 comprises a spiral or helical electrode element 307 that contacts the wall of the vasculature along one or more partial or complete oblique circumferences. The electrode element 307 may comprise a single continuous electrode over all or a portion of the spiral for formation of a continuous oblique treatment, and/or may comprise multiple discrete electrodes positioned along the spiral, e.g., for formation of a non-continuous circumferential treatment relative to both oblique and the normal planes of the vessel. Regardless of the form of the electrode element 307, the treatment zone(s) formed with the electrode may form a non-continuous circumferential treatment relative to the normal radial plane of the vasculature.

FIG. 9B illustrates an alternative embodiment of the apparatus and methods of FIG. 9A, in which the electrode element 307 comprises a double helix. This may facilitate formation of multiple, non-continuous treatment zones along one or more normal radial planes of the vessel. Continuous or non-continuous oblique treatments also may be achieved, while non-continuous normal circumferential treatments are achieved via superimposition of treatment at multiple locations (either discrete or continuous) along a lengthwise segment of the vasculature.

Figure 10A:
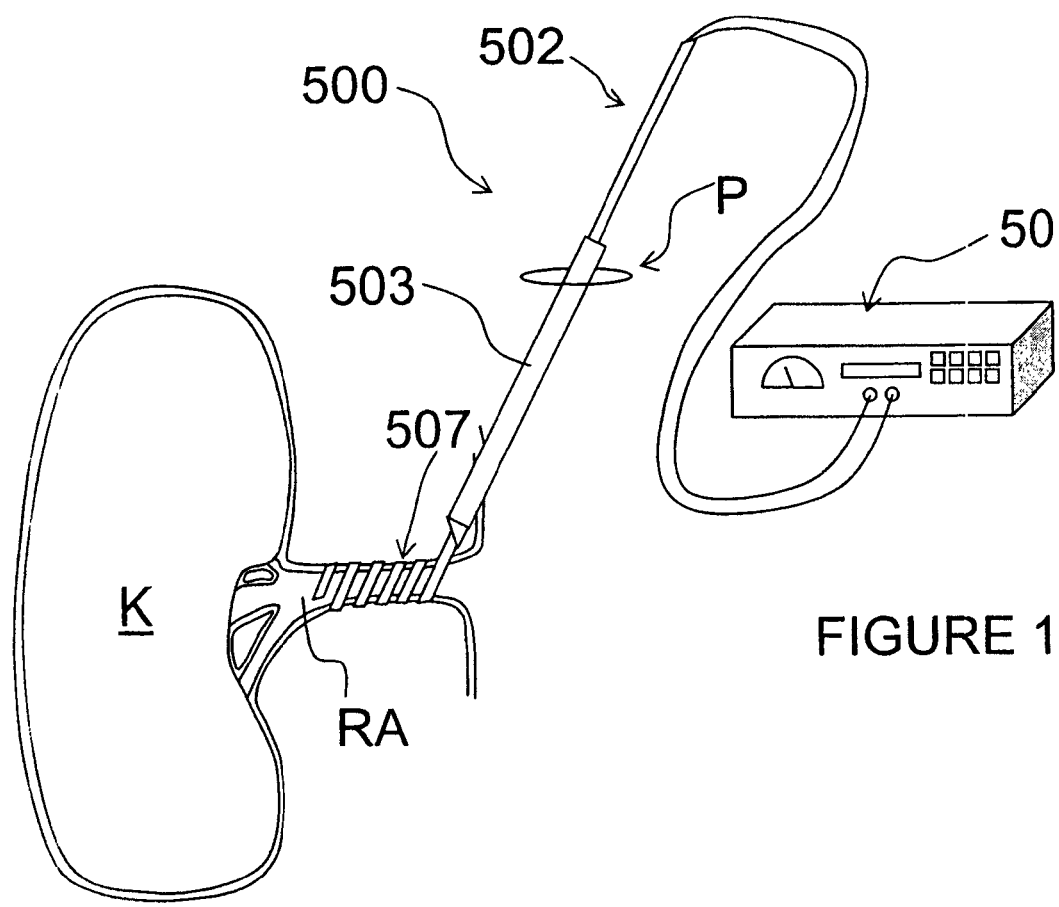
FIGS. 10A and 10B are schematic side views, partially in section, illustrating extravascular embodiments of methods and apparatus for non-continuous circumferential treatment of a body lumen, illustratively oblique circumferential treatment.
Figure 10B:
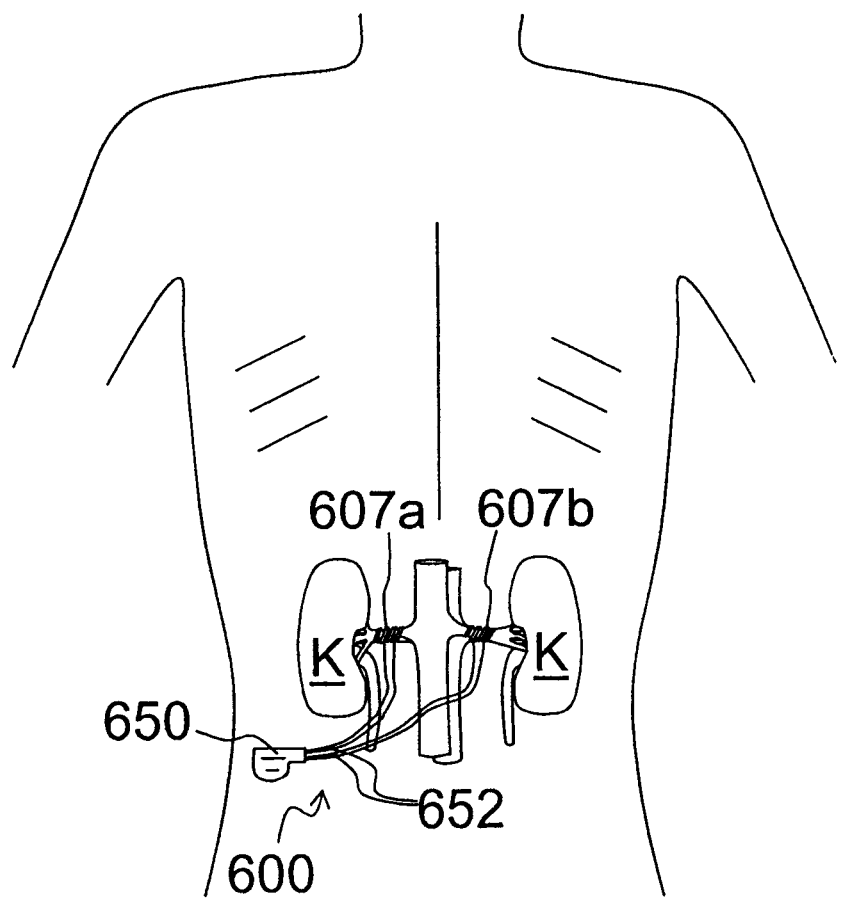

Referring now to FIGS. 10A and 10B, extravascular variations are described. FIG. 10A illustrates a percutaneous or transcutaneous extravascular variation having electrode(s) configured for temporary placement about the renal vasculature of the patient. FIG. 10B illustrates an implantable extravascular variation configured for prolonged placement within the patient. As will be apparent to those of skill in the art, a composite extravascular variation also may be provided having some elements configured for temporary placement and some elements configured for prolonged placement. In one such variation, one or more electrodes may be implanted within the patient, and a pulse generator or battery charging unit, etc., may be placed external to the patient and/or may be placed within the patient only temporarily during treatment, diagnostics, charging, etc.

The apparatus and methods of FIG. 10 illustratively are configured for formation of partially or completely continuous oblique circumferential treatments that are non-continuous relative to normal radial planes of the patient's vasculature. However, it should be understood that alternative extravascular embodiments may comprise non-continuous normal circumferential treatments that are non-continuous about both the normal and lengthwise dimensions of the vasculature, as opposed to just the normal dimension, i.e., that are also non-continuous about the oblique section. See, for example, the treatments defined by the apparatus and methods of FIGS. 2-7.

In FIG. 10A, apparatus 500 comprises needle or trocar 503 that forms percutaneous access site P. Catheter 502 is advanced through the trocar into proximity of the patient's renal artery RA. Electrode element 507 spirals about the renal artery for formation of an oblique circumferential treatment, as described with respect to FIG. 9A. Electrode element 507 is electrically coupled to field generator 50 for delivery of a desired electrical treatment. The apparatus 500 optionally may be removed from the patient, and the access site P closed, after formation of the oblique circumferential treatment.

FIG. 10B illustrates an extravascular embodiment that is fully implantable and illustratively is configured for bilateral treatment of nerves innervating both of the patient's kidney. It should be understood that any of the previously described embodiments also may be utilized for bilateral treatment, either concurrently or sequentially. Apparatus 600 comprises first and second spiral electrode elements 607a and 607b that spiral about the patient's renal arteries. The electrode elements are electrically coupled to implantable field generator 650, e.g., via tunneled leads 652, for formation of the previously described oblique circumferential treatment.

FIGS. 2-7 and 9-10 illustratively describe electrical methods and apparatus for circumferential treatment without formation of a continuous circumferential lesion positioned normal to the lengthwise axis of the patient's vasculature. However, it should be understood that alternative energy modalities, including magnetic, mechanical, thermal, chemical, nuclear/radiation, fluid, etc., may be utilized to achieve the desired circumferential treatment without circumferential lesion. Furthermore, although FIGS. 2-7 and 9 illustratively comprise fully intravascular positioning of the apparatus, it should be understood that all or a portion of the apparatus in any of the embodiments may be positioned extravascularly as in FIG. 10, optionally via implantation and/or via an intra-to-extravascular approach.

Although preferred illustrative variations of the present invention are described above, it will be apparent to those skilled in the art that various changes and modifications may be made thereto without departing from the invention. For example, although in the described embodiments of FIGS. 2-4 non-continuous circumferential treatment is achieved via superimposition of treatment at two locations, it should be understood that treatment at more than two locations may be superimposed to achieve the circumferential treatment, as described with respect to FIGS. 5A and 5B. Furthermore, although in the described embodiments the methods are conducted in a blood vessel, it should be understood that treatment alternatively may be conducted in other body lumens. It is intended in the appended claims to cover all such changes and modifications that fall within the true spirit and scope of the invention.

We claim:

1. An apparatus for renal denervation, the apparatus comprising:
    a catheter configured for intravascular placement within a renal blood vessel of a human patient;
    an expandable balloon at a distal portion of the catheter, wherein the expandable balloon is configured to transform between a delivery configuration and a deployed configuration sized to fit within the renal blood vessel; and
    a plurality of electrodes attached to the expandable balloon, wherein each electrode comprises at least one pair of bipolar contacts and is part of a flex circuit on a surface of the balloon configured to deliver thermal radio frequency (RF) energy in a bipolar fashion across an interior wall of the renal blood vessel to targeted renal nerves to achieve at least partial renal denervation, wherein, when the expandable balloon is in the deployed configuration, all of the electrodes are spaced apart from each other and arranged on an oblique circumference about the balloon that is not normal to a longitudinal axis thereof, and wherein each electrode occupies a distinct longitudinal position and a distinct radial position with respect to the longitudinal axis.

2. The apparatus of claim 1 wherein the plurality of electrodes comprises:

a first electrode configured to deliver thermal energy to create a first treatment zone along a lengthwise segment of the renal blood vessel; and a second electrode configured to deliver thermal energy to create a second treatment zone offset from the first treatment zone and along the same lengthwise segment of the renal blood vessel.

3. The apparatus of claim 1, further comprising an electric field generator external to the patient and configured to be electrically coupled to the electrodes, and wherein the electric field generator is configured to independently control each electrode.

4. The apparatus of claim 3 wherein the generator is configured to deliver thermal energy to the electrodes sequentially.

5. The apparatus of claim 3 wherein the generator is configured to deliver thermal energy to the electrodes concurrently.

6. The apparatus of claim 1 wherein the flex circuit terminates proximally of a distal end portion of the expandable balloon.

7. The apparatus of claim 1 wherein the expandable balloon is configured to position the electrodes in apposition with an interior wall of the renal blood vessel when the expandable balloon is in the deployed configuration.

8. The apparatus of claim 1 wherein, in the deployed configuration, the expandable balloon is sized to occlude the renal blood vessel.

9. The apparatus of claim 1 wherein each of the electrodes is dynamically assignable.

10. The apparatus of claim 1 wherein the plurality of electrodes comprises four or more electrodes.

11. The apparatus of claim 10 wherein the electrodes are equally spaced about a circumference of the expandable balloon.

12. The apparatus of claim 1 wherein at least one of the electrodes further comprises a sensor for monitoring and/or controlling effects of the thermal RF energy delivery.

13. The apparatus of claim 12 wherein the sensor comprises a temperature sensor.

14. The apparatus of claim 13 wherein the temperature sensor is configured to monitor temperature of the balloon, electrodes, and/or non-targeted tissue.

15. The apparatus of claim 12, further comprising a feedback control system configured to maintain or alter treatment in response to a monitored parameter from the sensors.

16. The apparatus of claim 1 wherein the catheter and expandable balloon are configured for placement within the renal blood vessel over a guidewire.

\* \* \* \* \*